(12) United States Patent
Bredno et al.

(10) Patent No.: US 11,615,532 B2
(45) Date of Patent: Mar. 28, 2023

(54) QUANTITATION OF SIGNAL IN STAIN AGGREGATES

(71) Applicant: Ventana Medical Systems, Inc., Tucson, AZ (US)

(72) Inventors: Joerg Bredno, Tucson, AZ (US); Auranuch Lorsakul, Tucson, AZ (US)

(73) Assignee: VENTANA MEDICAL SYSTEMS, INC., Tucson, AZ (US)

(*) Notice: Subject to any disclaimer, the term of this patent is extended or adjusted under 35 U.S.C. 154(b) by 0 days.

(21) Appl. No.: 17/586,982

(22) Filed: Jan. 28, 2022

(65) Prior Publication Data

US 2022/0148176 A1 May 12, 2022

Related U.S. Application Data

(63) Continuation of application No. PCT/EP2019/062296, filed on May 14, 2019.

(Continued)

(51) Int. Cl.
*G06T 7/00* (2017.01)
*G06T 7/62* (2017.01)
*G06T 7/194* (2017.01)

(52) U.S. Cl.
CPC ............ *G06T 7/0012* (2013.01); *G06T 7/194* (2017.01); *G06T 7/62* (2017.01); *G06T 2207/30024* (2013.01); *G06T 2207/30072* (2013.01)

(58) Field of Classification Search
CPC ......... G06T 7/0012; G06T 7/62; G06T 7/194; G06T 2207/30024; G06T 2207/30072;

(Continued)

(56) References Cited

U.S. PATENT DOCUMENTS 5,650,327 A 7/1997 Copeland
5,654,200 A 8/1997 Copeland (Continued)

FOREIGN PATENT DOCUMENTS

WO 2001020044 A2 3/2001
WO WO-0120044 A2 * 3/2001 ........... C12Q 1/6809

(Continued)

OTHER PUBLICATIONS

Achanta, Radhakrishna et al. "SLIC Superpixels Compared to State-of-the-Art Superpixel Methods"; IEEE Transactions on Pattern Analysis and Machine Intelligence; vol. 34; No. 11; Nov. 2012; pp. 2274-2281.

(Continued)

*Primary Examiner* — Vu Le
*Assistant Examiner* — Winta Gebreslassie
(74) *Attorney, Agent, or Firm* — Kilpatrick Townsend & Stockton LLP

(57) ABSTRACT

The present application provides for systems and methods for detecting and estimating signals corresponding to one or more biomarkers in biological samples stained for the presence of protein and/or nucleic acid biomarkers. On particular aspect is directed to a method of estimating an amount of signal corresponding to at least one biomarker in an image of a biological sample. The method includes detecting isolated spots in a first image, deriving an optical density value of a representative isolated spot based on signal features from the detected isolated spots, estimating a number of predictive spots in signal aggregates in each of a plurality of sub-regions based on the derived optical density value of the representative isolated spot, and storing the estimated number of predictive spots and detected isolated spots in each of the plurality of generated sub-regions in a database.

17 Claims, 28 Drawing Sheets
(17 of 28 Drawing Sheet(s) Filed in Color)

WS – Wholeslide

Related U.S. Application Data

(60) Provisional application No. 62/671,825, filed on May 15, 2018.

(58) Field of Classification Search
CPC .......... G06T 2207/10056; G16H 50/20; G16H 30/40; G02B 21/008
See application file for complete search history.

(56) References Cited

U.S. PATENT DOCUMENTS

| | | | |
|---|---|---|---|
| 6,296,809 B1 | 10/2001 | Richards | |
| 6,352,861 B1 | 3/2002 | Copeland | |
| 6,827,901 B2 | 12/2004 | Copeland | |
| 6,943,029 B2 | 9/2005 | Copeland | |
| 7,087,379 B2 | 8/2006 | Light | |
| 8,236,502 B2 | 8/2012 | Utermohlen | |
| 9,378,407 B2 | 6/2016 | Zhang et al. | |
| 9,972,087 B2 | 5/2018 | Isoda et al. | |
| 10,656,092 B2 | 5/2020 | Ozaki et al. | |
| 2002/0186874 A1* | 12/2002 | Price | G01N 15/147 382/173 |
| 2003/0211630 A1 | 11/2003 | Richards | |
| 2004/0052685 A1 | 3/2004 | Richards | |
| 2011/0151502 A1 | 6/2011 | Kendall et al. | |
| 2012/0163681 A1* | 6/2012 | Lohse | G01N 21/6456 382/128 |
| 2014/0178169 A1 | 6/2014 | Hebert | |
| 2014/0377753 A1 | 12/2014 | Bamford | |
| 2016/0370565 A1 | 12/2016 | Bredno et al. | |
| 2017/0154420 A1 | 6/2017 | Barnes | |
| 2017/0323148 A1* | 11/2017 | Sarkar | G06T 7/0012 |
| 2018/0204085 A1* | 7/2018 | Chennubhotla | G16H 50/20 |

FOREIGN PATENT DOCUMENTS

| | | |
|---|---|---|
| WO | 2009117682 A1 | 9/2009 |
| WO | 2011049608 | 4/2011 |
| WO | 2013113707 A1 | 8/2013 |
| WO | 2014195193 | 12/2014 |
| WO | 2015124772 | 8/2015 |
| WO | 2016087589 A1 | 6/2016 |
| WO | 2016150873 A1 | 9/2016 |

OTHER PUBLICATIONS

Avidan, Shai et al.; "Seam carving for content-aware image resizing"; ACM Transactions on Graphics (SIGGRAPH), 26(3), 2007; 9 pages.
Bankman, Isaac N.; Handbook of Medical Imaging, Processing and Analysis; Academic Press; 2000; chapter 2; pp. 19-33.
10$^{th}$ European Conference on Computer Vision (ECCV); Marseille, France; Oct. 12-18, 2008.
Gonzalez, Rafael C. et al.; "Digital Image Processing"; Third Edition; Chapter 10; p. 689.
International Application No. PCT/EP2019/062296 received an International Search Report and Written Opinion, dated Jun. 28, 2019, 11 pages.
JP Application No. JP2020-564469 received an Office Action, dated Jan. 26, 2022, 9 pages.
Lawson, Charles L. et al.; "Solving Least Squares Problems"; 1974; Chapter 23; p. 161.
Levinshtein, Alex et al.; "TurboPixels: Fast Superpixels Using Geometric Flows"; IEEE Transactions on Pattern Analysis and Machine Intelligence (PAMI); Dec. 2009; vol. 31; No. 12; pp. 2290-2297.
Moore, Alastair P. et al.; "Superpixel Lattices"; IEEE Conference on Computer Vision and Pattern Recognition, Jun. 23, 2008, pp. 1-8.
Shi, Jianbo et al; "Normalized Cuts and Image Segmentation"; IEEE Transactions on Pattern Analysis and Machine Intelligence (PAMI); Aug. 2000; vol. 22; No. 8; pp. 888-905.
Zimmermann, Timo; "Spectral Imaging and Linear Unmixing in Light Microscopy"; Adv Biochem Engin/Biotechnology; 2005; 95; pp. 245-265.
Achanta et al., SLIC Superpixels Compared to State-of-the-art Superpixel Methods, Journal of Latex Class Files, vol. 6, No. 1, Dec. 2011, pp. 1-8.
International Application No. PCT/EP2019/062296, International Preliminary Report on Patentability dated Nov. 26, 2020, 8 pages.
Vedaldi et al., Quick Shift and Kernel Methods for Mode Seeking, In European Conference on Computer Vision, Oct. 2008, 14 pages.

* cited by examiner

FIG. 10B
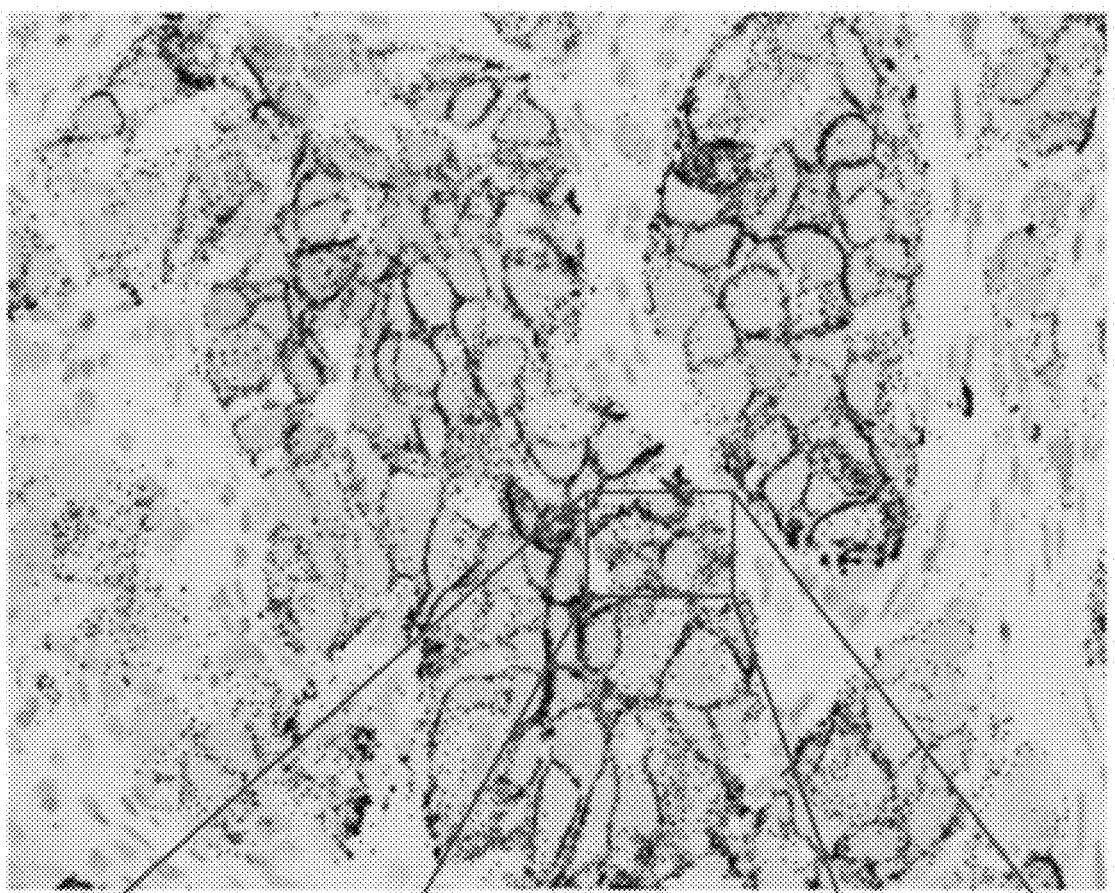
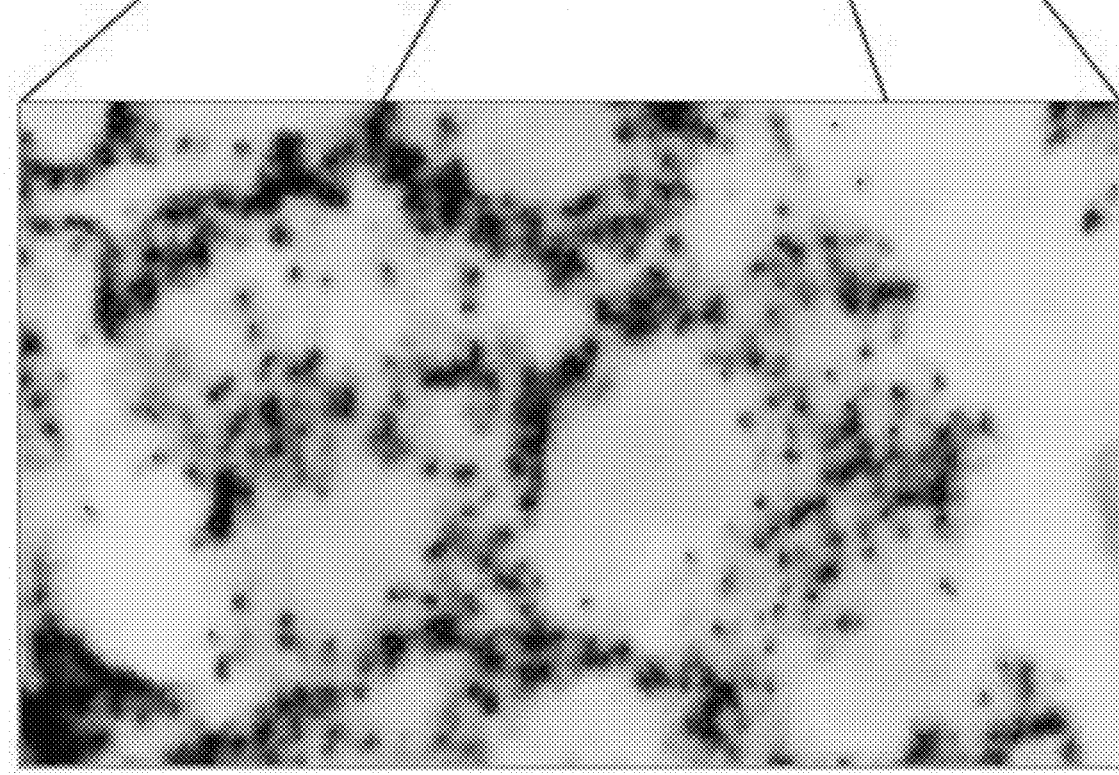
FIG. 10C

1610

QUANTITATION OF SIGNAL IN STAIN AGGREGATES

CROSS REFERENCE TO RELATED APPLICATIONS

The present application is a continuation of PCT/EP2019/062296, filed on May 14, 2019, which claims the benefit of U.S. Provisional Patent Application No. 62/671,825, filed on May 15, 2018, the disclosure of which is hereby incorporated by reference herein in its entirety.

BACKGROUND OF THE DISCLOSURE

Digital pathology involves scanning of whole histopathology or cytopathology glass slides into digital images interpretable on a computer screen. These images are to be processed subsequently by an imaging algorithm or interpreted by a pathologist. In order to examine tissue sections (which are virtually transparent), tissue sections are prepared using colored histochemical stains that bind selectively to cellular components. Color-enhanced, or stained, cellular structures are used by clinicians or a computer-aided diagnosis (CAD) algorithm to identify morphological markers of a disease, and to proceed with therapy accordingly. Observing the assay enables a variety of processes, including diagnosis of disease, assessment of response to treatment, and development of new drugs to fight disease.

Immunohistochemical (IHC) slide staining can be utilized to identify proteins in cells of a tissue section and hence is widely used in the study of different types of cells, such as cancerous cells and immune cells in biological tissue. Thus, IHC staining may be used in research to understand the distribution and localization of the differentially expressed biomarkers of immune cells (such as T-cells or B-cells) in a cancerous tissue for an immune response study. For example, tumors often contain infiltrates of immune cells, which may prevent the development of tumors or favor the outgrowth of tumors.

In-situ hybridization (ISH) can be used to look for the presence of a genetic abnormality or condition such as amplification of cancer causing genes specifically in cells that, when viewed under a microscope, morphologically appear to be malignant. Unique nucleic acid sequences occupy precise positions in chromosomes, cells and tissues and in-situ hybridization allows the presence, absence and/or amplification status of such sequences to be determined without major disruption of the sequences. ISH employs labeled DNA or RNA probe molecules that are anti-sense to a target gene sequence or transcript to detect or localize targeted nucleic acid target genes within a cell or tissue sample. ISH is performed by exposing a cell or tissue sample immobilized on a glass slide to a labeled nucleic acid probe which is capable of specifically hybridizing to a given target gene in the cell or tissue sample. Several target genes can be simultaneously analyzed by exposing a cell or tissue sample to a plurality of nucleic acid probes that have been labeled with a plurality of different nucleic acid tags. By utilizing labels having different emission wavelengths, simultaneous multicolored analysis may be performed in a single step on a single target cell or tissue sample.

BRIEF SUMMARY OF THE DISCLOSURE

Historically, the clinical evaluation of proteins and nucleic acids in tissue has relied upon in situ immunoenzymatic detection methods. For example, detection of B cell clonality is useful for assisting in the diagnosis of B cell lymphomas and the clonality assessment can be accomplished through the evaluation of KAPPA and LAMBDA light chain expression. As seen in FIG. 8A, tonsil tissue stained for KAPPA mRNA detected may be detected with silver (Ag) (appears as a black in color) and LAMBDA mRNA may be detected with Tyramide-sulforhodamine (appears as a purple color). The presence of the signal of interest appears as tiny spots (e.g. discrete dots) and these spots may accumulate to form larger regions of aggregate signal (hereinafter "signal aggregate blobs" or "blobs") depending on the copy number of mRNA in the cells. By way of example, plasma cells have approximately 100,000 mRNA copies per cell, and therefore signal in those cells may appear as blobs.

Quantitative ISH and IHC analysis is useful in clinical evaluation; however, it is not widely performed because of the limitations of existing technology. An automated technique for estimating an amount of signal in signal aggregate blob may facilitate enhanced clinical interpretation of stained biological samples and enable samples to be interpreted more quickly and accurately. In view of the foregoing, Applicant has developed an image-analysis system and method that enables the detection and quantification of the number of protein or nucleic acid signals present in stained samples.

In one aspect of the present disclosure is a method of estimating an amount of signal corresponding to at least one biomarker in an image of a biological sample comprising: detecting isolated spots in a first image (e.g. an unmixed image channel image corresponding to signals from a first biomarker); deriving an optical density value of a representative isolated spot (e.g. based on computed signal features or characteristics from the detected isolated spots); and estimating a number of predictive spots in signal aggregates in each of a plurality of sub-regions based on the derived optical density value of the representative isolated spot. In some embodiments, the method further comprises calculating a total of number of spots in a sub-region by combining a number of detected isolated spots and the estimated number of predictive spots in signal aggregates in each of the sub-regions.

In some embodiments, the number of predictive spots in the signal aggregates in each of the plurality of the sub-regions is estimated by calculating a quotient of a total optical density of the signal aggregates in one of the sub-regions divided by the derived optical density of the representative isolated spot. In some embodiments, the total optical density of the signal aggregates in one of the sub-regions is a measured value. In some embodiments, optical density of the representative isolated spot is derived by: (i) generating histogram plots from computed descriptive signal features of all detected isolated spots; (ii) extracting size and intensity parameters from the histogram plots; (iii) calculating an area measurement from the extracted size parameters; and (iv) multiplying the extracted intensity parameter by the calculated area measurement. In some embodiments, the computed descriptive signal features are derived by characterizing signal features (e.g. mean, standard deviation, full-width at half maximum, or size) from the detected isolated spots. In some embodiments, the computed descriptive signal features comprise spot intensity, spot blurriness, spot roundness, and spot size. In some embodiments, the descriptive signal features are computed using a 1-D Gaussian function fitting method in an image patch having a predetermined size (e.g. 7×7 pixels).

In some embodiments, the size parameter is a mode of a radius from a full width at half maximum histogram. In some embodiments, the size parameter is a mean of a radius from a full width at half maximum histogram. In some embodiments, the intensity parameter is a uniform intensity metric. In some embodiments, the intensity parameter is a non-uniform intensity metric. In some embodiments, the uniform intensity metric is a mode of an intensity value derived from an intensity histogram. In some embodiments, the uniform intensity metric is a mean of an intensity value derived from an intensity histogram. In some embodiments, the uniform intensity metric is a weighted average intensity derived from an intensity histogram. In some embodiments, the non-uniform intensity metric is derived from a blurriness histogram computed from a blurriness signal feature of each of the detected isolated spots.

In some embodiments, the estimation of the number of predictive spots is performed using a second image, the second image being substantially free from signals corresponding to the detected isolated spots. In some embodiments, the second image is a residual image, as described herein. In some embodiments, the second image is derived by (i) generating a foreground segmentation mask based on the detected isolated spots in the first image; and (ii) filtering the first image with the generated foreground segmentation mask. In some embodiments, the second image is generated by (i) generating an isolated spots image including only the detected isolated spots from the first image; and (ii) subtracting the isolated spots image from the first image. In some embodiments, the second region is segmented into a plurality of sub-regions.

In some embodiments, each sub-region of the plurality of sub-regions has pixels which are substantially uniform in at least one of biomarker staining intensity, biomarker staining presence, and local biomarker staining texture. In some embodiments, each of the plurality of sub-regions are superpixels. In some embodiments, the superpixels are derived by (i) grouping pixels with local k-means clustering; and (ii) using a connected components algorithm to merge small isolated regions into nearest large superpixels. In some embodiments, a 70×70 pixel size was used along with a regularization parameter of about 10 to generate the superpixels. In some embodiments, segmentation is performed on the second image noted above. In some embodiments, the sub-regions are derived by overlaying a sampling grid onto the second image, the sampling grid defining non-overlapping areas having a predetermined size and shape (e.g. simple object shapes such as squares, circles, etc.), e.g. an area having a size of about 70 pixels by 70 pixels to about 200 pixels by about 200 pixels. In some embodiments, the method further comprises repeating at least some of the aforementioned steps to estimate signals corresponding to a second biomarker.

In some embodiments, the method of estimating signal corresponding to a second biomarker comprises detecting isolated spots in an unmixed image channel image corresponding to signals from a second biomarker; deriving an optical density value of a representative isolated spot (e.g. based on computed signal features from the detected isolated spots); and estimating a number of predictive spots in signal aggregates in each of a plurality of sub-regions based on the computed descriptive signal features of the detected isolated spots. In some embodiments, the estimation of the number of predictive spots corresponding to the second biomarker is conducted using an image derived from the unmixed image channel image having isolated spots and signal aggregates, where signal from the detected isolated spots is removed, corresponding to the second biomarker.

In some embodiments, the biological sample is stained for the presence of one or more protein biomarkers, e.g. HER2 protein biomarkers. In some embodiments, the biological is stained for the presence of one or more nucleic acid biomarkers. In some embodiments, the biological sample is stained for the presence of one or more mRNA sequences (e.g. one or more KAPPA mRNA sequences and/or one or more LABDA mRNA sequences). In some embodiments, each of the one or more KAPPA mRNA sequences are detected using the same reporter moiety (e.g. a silver chromogen). In some embodiments, each of the one or more LAMBDA mRNA sequences are detected using the same reporter moiety (e.g. a purple chromogen).

In some embodiments, the method further comprises storing the estimated number of predictive spots and the detected isolated spots in each of the plurality of generated sub-regions of an entire whole slide image in a database. In some embodiments, the method further comprises using the stored data to generate an overlay which may be superimposed on the input image (e.g. a whole slide image or a portion thereof). In some embodiments, the method further comprises generating an image overlay independently visualizing the number of detected isolated spots and the estimated number of predictive spots in each sub-region. In some embodiments, the method further comprises generating an image overlay visualizing the total amount of signal from the number of estimated predictive spots in each sub-region and the detected isolated spots. In some embodiments, the visualization includes information pertaining to more than one biomarker.

In another aspect of the present disclosure is method of estimating an amount of signal corresponding to at least one biomarker in an image of a biological sample comprising: detecting isolated spots in an input image (e.g. a simplex image or an unmixed image channel image derived from a multiplex image); computing descriptive signal features from the detected isolated spots; and estimating a number of predictive spots in signal aggregates in each of a plurality of sub-regions in a second image based on the computed descriptive signal features of the detected isolated spots. In some embodiments, the method further comprises calculating a total of number of spots in a sub-region by combining the number of detected isolated spots and the estimated number of predictive spots in signal aggregates in each of the sub-regions.

In some embodiments, the method further comprises storing the estimated number of predictive spots and/or the detected isolated spots in each of the plurality of generated sub-regions and/or in a whole slide image in a database. In some embodiments, the number of predictive spots in the signal aggregates in each of the plurality of the sub-regions is estimated by: (i) deriving an optical density of a representative isolated spot, the optical density of the representative isolated spot derived from the computed descriptive signal features; and (ii) calculating a quotient of a total optical density of the signal aggregates in one of the sub-regions of the second image divided by the derived optical density of the representative isolated spot. In some embodiments, the optical density of the representative isolated spot is derived by: (i) generating histogram plots from each of the computed descriptive signal features; (ii) extracting size and intensity parameters from the histogram plots; (iii) calculating an area measurement from the extracted size parameters; and (iv) multiplying the extracted intensity parameter by the calculated area measurement. In some embodiments, the computed descriptive signal features are derived by characterizing signal features (e.g. mean, standard deviation, full-width at half maximum, or size) from the detected isolated spots. In some embodiments, the intensity parameters are selected from uniform intensity metrics and non-uniform intensity metrics. In some embodiments, the computed descriptive signal features are size, blurriness, intensity, and roundness.

In another aspect of the present disclosure is a method of estimating an amount of signal corresponding to at least one biomarker in an image of a biological sample comprising: detecting signals corresponding to single gene copies in a first image (e.g. an unmixed image channel image corresponding to signals from a first biomarker); deriving an optical density value of a representative signal corresponding to a single gene copy based on computed signal features from all detected signals corresponding to single gene copies in the first image; and estimating a number of predictive signals (corresponding to a plurality of gene copies) in signal blobs in each of a plurality of sub-regions in a second image (e.g. an image where the detected isolated spots do not substantially contribute to the signal within the signal aggregates) based on the derived optical density value of the representative signal corresponding to a single gene copy. In some embodiments, optical density of the representative signal corresponding to a single gene copy is derived by: (i) generating histogram plots from at least two computed descriptive signal features; (ii) extracting size and intensity parameters from the histogram plots; (iii) calculating an area measurement from the extracted size parameters; and (iv) multiplying the extracted intensity parameter by the calculated area measurement. In some embodiments, the intensity parameters are selected from uniform intensity metrics and non-uniform intensity metrics. In some embodiments, the computed descriptive signal features are size, blurriness, intensity, and roundness. In some embodiments, the method further comprises generating an overlay based on the estimated number of predictive spots and/or the detected isolated spots. In some embodiments, the method further comprises repeating at least some of the aforementioned steps for another gene (by way of example only, performing the method a first time for KAPPA mRNA and a second time for LAMBDA mRNA).

In another aspect of the present disclosure is a method of estimating an amount of signal corresponding to at least one biomarker in an image of a biological sample comprising: detecting isolated spots in a first image (e.g. an unmixed image channel image corresponding to signals from a first biomarker); deriving an optical density value of a representative isolated spot based on computed signal features from the detected isolated spots; generating a residual image derived from the first image that is substantially free of signals corresponding to the detected isolated spots; segmenting the residual image into a plurality of sub-regions; and estimating a number of predictive spots in signal aggregates in each of a plurality of sub-regions based on the derived optical density of the representative isolated spot. In some embodiments, the first image is stained for the presence of at least one nucleic acid biomarker. In other embodiments, the first image is stained for the presence of at least one protein biomarker. In some embodiments, the computed descriptive signal features are derived by characterizing signal features (e.g. mean, standard deviation, full-width at half maximum, or size) from the detected isolated spots. In some embodiments, the computed descriptive signal features comprise spot intensity, spot blurriness, spot roundness, and spot size.

In another aspect of the present disclosure is a system for estimating an amount of one or more signals in a biological sample, the one more signals corresponding to stained targets (e.g. proteins, nucleic acids, etc.) in a biological sample, the system comprising: (i) one or more processors, and (ii) a memory coupled to the one or more processors, the memory to store computer-executable instructions that, when executed by the one or more processors, cause the system to perform operations comprising: detecting isolated spots in a first image (e.g. an unmixed image channel image corresponding to signals from a first biomarker); deriving an optical density value of a representative isolated spot based on computed signal features from the detected isolated spots; and estimating a number of predictive spots in signal aggregates in each of a plurality of sub-regions in a second image (e.g. an image where the detected isolated spots do not substantially contribute to the signal within the signal aggregates) based on the derived optical density value of the representative isolated spot. In some embodiments, the system further comprises instructions for calculating a total of number of spots in a sub-region by combining a number of detected isolated spots and the estimated number of predictive spots in signal aggregates in each of the sub-regions.

In some embodiments, the number of predictive spots in the signal aggregates in each of the plurality of the sub-regions is estimated by calculating a quotient of a total optical density of the signal aggregates in one of the sub-regions of the second image divided by the derived optical density of the representative isolated spot. In some embodiments, optical density of the representative isolated spot is derived by: (i) generating histogram plots from each of the computed descriptive signal features; (ii) extracting size and intensity parameters from the histogram plots; (iii) calculating an area measurement from the extracted size parameters; and (iv) multiplying the extracted intensity parameter by the calculated area measurement. In some embodiments, the computed descriptive signal features are derived from signal characteristics of each detected isolated spot, including mean, standard deviation, full-width at half maximum or size. In some embodiments, the size parameter is a mode of a radius from a full width at half maximum histogram. In some embodiments, the intensity parameter is a uniform intensity metric or a non-uniform intensity metric. In some embodiments, the uniform intensity metric is a mode of an intensity value derived from an intensity histogram. In some embodiments, the uniform intensity metric is a mean of an intensity value derived from an intensity histogram. In some embodiments, the uniform intensity metric is a weighted average intensity derived from an intensity histogram. In some embodiments, the non-uniform intensity metric is derived from a blurriness histogram computed from a blurriness signal feature of each of the detected isolated spots.

In some embodiments, the computed descriptive signal features comprise spot intensity, spot blurriness, spot roundness, and spot size. In some embodiments, the descriptive signal features are computed using a 1-D Gaussian function fitting method in an image patch having a predetermined size, e.g. 7×7 pixels.

In some embodiments, the second image is derived by (i) generating a foreground segmentation mask based on the detected isolated spots in the first image; and (ii) filtering the first image with the generated foreground segmentation mask. In some embodiments, the second image is generated by (i) generating an isolated spots image including only the detected isolated spots from the first image; and (ii) subtracting the isolated spots image from the first image.

In some embodiments, each sub-region of the plurality of sub-regions has pixels which are substantially uniform in at least one of biomarker staining intensity, biomarker staining presence, and local biomarker staining texture. In some embodiments, each of the plurality of sub-regions are superpixels. In some embodiments, the superpixels are derived by (i) grouping pixels with local k-means clustering; and (ii) using a connected components algorithm to merge small isolated regions into nearest large superpixels. In some embodiments, the sub-regions are derived by overlaying a sampling grid onto the second image, the sampling grid defining non-overlapping areas having a predetermined size and shape.

In another aspect of the present disclosure is a system for estimating an amount of one or more signals in a biological sample, the one more signals corresponding to stained targets (e.g. proteins, nucleic acids, etc.) in a biological sample, the system comprising: (i) one or more processors, and (ii) a memory coupled to the one or more processors, the memory to store computer-executable instructions that, when executed by the one or more processors, cause the system to perform operations comprising: detecting isolated spots in a first image (e.g. an unmixed image channel image corresponding to signals from a first biomarker); computing descriptive signal features from all detected isolated spots; and estimating a number of predictive spots in signal aggregates in each of a plurality of sub-regions in a second image (e.g. an image where the detected isolated spots do not substantially contribute to the signal within the signal aggregates) based on the computed descriptive signal features. In some embodiments, the number of predictive spots in the signal aggregates in each of the plurality of the sub-regions is estimated by: (i) deriving an optical density of a representative isolated spot, the optical density of the representative isolated spot derived from the computed descriptive signal features; and (ii) calculating a quotient of a total optical density of the signal aggregates in one of the sub-regions of the second image divided by the derived optical density of the representative isolated spot. In some embodiments, the optical density of the representative isolated spot is derived by: (i) generating histogram plots from each of the computed descriptive signal features; (ii) extracting size and intensity parameters from the histogram plots; (iii) calculating an area measurement from the extracted size parameters; and (iv) multiplying the extracted intensity parameter by the calculated area measurement. In some embodiments, the intensity parameter is a uniform intensity metric or a non-uniform intensity metric. In some embodiments, the size parameter is a mode of a radius from a full width at half maximum histogram. In some embodiments, the first image is a first unmixed image channel image corresponding to signals from a first biomarker. In some embodiments, the computed descriptive signal features are derived from signal characteristics of each detected isolated spot, including mean, standard deviation, full-width at half maximum or size. In some embodiments, the computed descriptive signal features comprise spot intensity, spot blurriness, spot roundness, and spot size. In some embodiments, the descriptive signal features are computed using a 1-D Gaussian function fitting method in an image patch having a predetermined size. In some embodiments, the estimation of the number of the predictive spots in the signal aggregates is performed using a second image which is substantially free from signals corresponding to the detected isolated spots.

In another aspect of the present disclosure is a non-transitory computer-readable medium storing instructions for estimating amounts of different signals in a stained biological sample, comprising: detecting isolated spots in a first image (e.g. an unmixed image channel image corresponding to signals from a first biomarker); deriving an optical density value of a representative isolated spot based on computed signal features from the detected isolated spots; and estimating a number of predictive spots in signal aggregates in each of a plurality of sub-regions in a second image (e.g. an image where the detected isolated spots do not substantially to the signal within the signal aggregates) based on the derived optical density value of the representative isolated spot. In some embodiments, the optical density of the representative isolated spot is derived by: (i) generating histogram plots from each of the signal feature from the detected isolated spots; (ii) extracting size and intensity parameters from the histogram plots; (iii) calculating an area measurement from the extracted size parameters; and (iv) multiplying the extracted intensity parameter by the calculated area measurement. In some embodiments, the isolated spots are detected using a shape-detector having a disk-like shape. In some embodiments, the sub-regions are superpixels. In some embodiments, the superpixels are derived by (i) grouping pixels with local k-means clustering; and (ii) using a connected components algorithm to merge small isolated regions into nearest large superpixels. In some embodiments, the number of predictive spots in the signal aggregates in each of the plurality of the sub-regions is estimated by calculating a quotient of a total optical density of the signal aggregates in one of the sub-regions divided by the derived optical density of the representative isolated spot. In some embodiments, the total optical density of the signal aggregates is a measured value. In some embodiments, the signals correspond to at least two nucleic acid biomarkers. In some embodiments, the signals correspond to at least one protein biomarker. In some embodiments, the non-transitory computer-readable medium further comprises instructions for unmixing an input image. In some embodiments, the non-transitory computer-readable medium further comprises instructions for segmenting an input image, e.g. an unmixed image channel image, into a plurality of sub-regions. In some embodiments, the non-transitory computer-readable medium further comprises instructions for generating superpixels. In some embodiments, the non-transitory computer-readable medium further comprises instructions for generating a second image that does not substantially include the signals from the detected isolated spots. In some embodiments, the non-transitory computer-readable medium further comprises instructions for generating a visualization and superimposing the generated visualization onto an input image. In some embodiments, the non-transitory computer-readable medium further comprises instructions for combining generated data from at least two image tiles, each image tile corresponding to a portion of a whole slide image and combining the data from the at least two tiles.

BRIEF DESCRIPTION OF THE FIGURES

The patent or application file contains at least one drawing executed in color. Copies of this patent or patent application publication with color drawing(s) will be provided by the Office upon request and payment of the necessary fee. For a general understanding of the features of the disclosure, reference is made to the drawings. In the drawings, like reference numerals have been used throughout to identify identical elements.

FIGS. 10B and 10C illustrate the result of spot detection of the protein biomarker from FIG. 10A.

DETAILED DESCRIPTION

Figure 1:
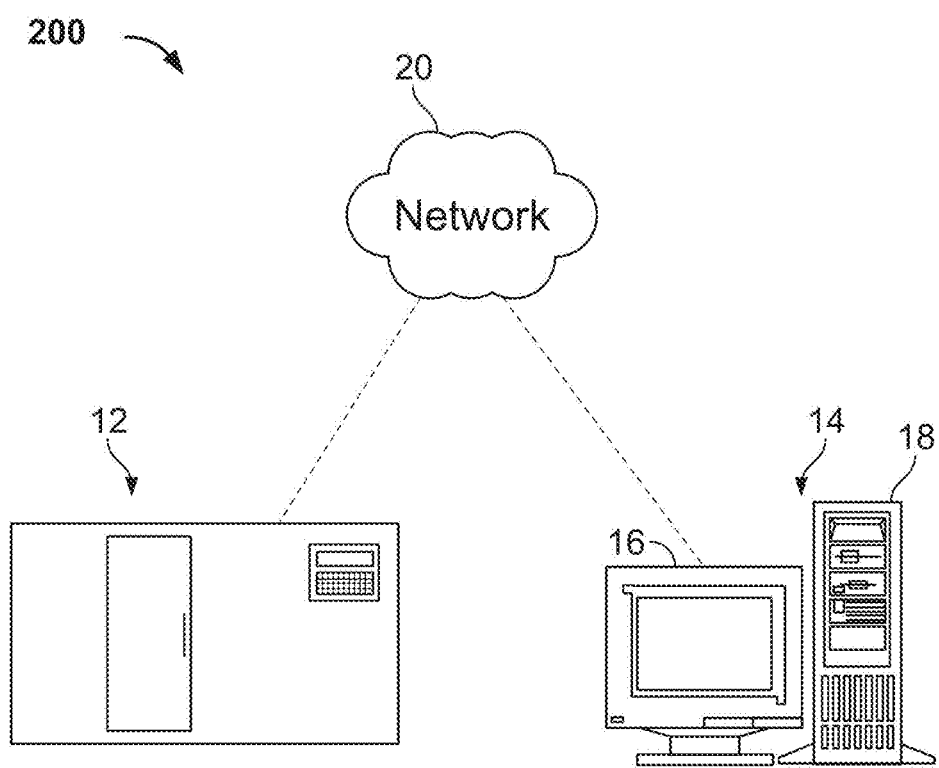
FIG. 1 illustrates a representative digital pathology system including an image acquisition device and a computer system, in accordance with some embodiments.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of" "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "biological sample," "tissue sample," "specimen" or the like refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "blob" refers to a region in a digital image that differs in properties, such as brightness or color, compared to surrounding regions. For example, a blob may be a set of adjacent pixels having a particular intensity value range.

A "foreground segmentation mask" is, for example, an image mask created by a segmentation algorithm that allows separating one or more pixel blobs (to be used as "foreground pixels") from other pixels (constituting the "background"). For example, the foreground segmentation mask may be generated by a nuclear segmentation algorithm and the application of the foreground segmentation mask on an image depicting a tissue section may allow identification of nuclear blobs in an image.

As used herein, the term "image data" encompasses raw image data acquired from the biological tissue sample, such as by means of an optical sensor or sensor array, or pre-processed image data. In particular, the image data may comprise a pixel matrix.

As used herein, the terms "image," "image scan," or "scanned image" encompasses raw image data acquired from the biological tissue sample, such as by means of an optical sensor or sensor array, or pre-processed image data. In particular, the image data may comprise a pixel matrix.

As used herein, the terms "multi-channel image" or "multiplex image" encompasses a digital image obtained from a biological tissue sample in which different biological structures, such as nuclei and tissue structures, are simultaneously stained with specific fluorescent dyes, quantum dots, chromogens, etc., each of which fluoresces or are otherwise detectable in a different spectral band thus constituting one of the channels of the multi-channel image.

As used herein, the terms "probe" or "oligonucleotide probe" refers to a nucleic acid molecule used to detect a complementary nucleic acid target gene.

As used herein, the term "slide" refers to any substrate (e.g., substrates made, in whole or in part, glass, quartz, plastic, silicon, etc.) of any suitable dimensions on which a biological specimen is placed for analysis, and more particularly to a "microscope slide" such as a standard 3 inch by 1 inch microscope slide or a standard 75 mm by 25 mm microscope slide. Examples of biological specimens that can be placed on a slide include, without limitation, a cytological smear, a thin tissue section (such as from a biopsy), and an array of biological specimens, for example a tissue array, a cellular array, a DNA array, an RNA array, a protein array, or any combination thereof. Thus, in one embodiment, tissue sections, DNA samples, RNA samples, and/or proteins are placed on a slide at particular locations. In some embodiments, the term slide may refer to SELDI and MALDI chips, and silicon wafers.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least $10^3$ M-1 greater, $10^4$ M-1 greater or $10^5$ M-1 greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

As used herein, the terms "stain," "staining," or the like as used herein generally refers to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cyto skeleton) in the biological specimen. For example, staining can provide contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system can be used to visualize an outline of a cell. Other staining performed by the system may rely on certain cell components (such as molecules or structures) being stained without or with relatively little staining other cell components. Examples of types of staining methods performed by the system include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

As used herein, the term "target" refers to any molecule for which the presence, location and/or concentration is or can be determined. Examples of target molecules include proteins, nucleic acid sequences, and haptens, such as haptens covalently bonded to proteins. Target molecules are typically detected using one or more conjugates of a specific binding molecule and a detectable label.

Overview

The present disclosure provides for systems and methods for detecting and estimating signals corresponding to one or more biomarkers in biological samples stained for the presence of protein and/or nucleic acid biomarkers. In some embodiments, the present disclosure enables an accurate estimation, i.e. quantitation, of an amount of signal corresponding to one or more biomarkers in signal aggregate blobs (e.g. in areas of dense biomarker stain).

In some embodiments, the systems and methods described herein facilitate the detection and counting of spot signals from individual isolated spots and from signal aggregate blobs that clump together in in situ hybridization (ISH) (e.g. from high gene copy numbers, etc.) and immunohistochemistry (IHC) images. The systems and methods disclosed herein enable the detection and characterization of isolated spot signals (e.g. representing, for example, single gene copies or single protein targets), and then applies the derived characteristics of the detected isolated spots to detect and estimate the number of the spots in the form of aggregate signals (i.e. in signal aggregate blobs). As a result, the total number of the spots for both isolated spots and aggregate blobs can be reported, and such quantities may be correlated to gene copy number (mRNA copies) or protein target quantities.

It is believed that the systems and methods described herein enable quantification of signal where there is quite a large amount of biomarker signal congregated in a small region, such as when there is the presence of a large number of gene copies in a cell. While the methods suited herein are suitable for use in detecting and estimating signals associated with both protein and nucleic acid biomarkers, the systems and methods are particularly suitable for the elucidation of signal quantities when large amounts of gene copies are present in a small area of a biological sample.

At least some embodiments of the present disclosure relate to computer systems and methods for analyzing digital images captured from biological samples, including tissue samples, stained with one or more primary stains (e.g. hematoxylin and eosin (H&E)) and one or more detection probes (e.g. probes containing a specific binding entity which facilitates the labeling of targets within the sample). While examples herein may refer to specific tissues and/or the application of specific stains or detection probes for the detection of certain markers (and hence diseases), the skilled artisan will appreciate that different tissues and different stains/detection probes may be applied to detect different markers and different diseases. For example, although certain examples may refer to quantifying an amount of signal corresponding to two different mRNA probes (or a series of mRNA probes having varying sequences), the systems and methods described herein may be applied to detect and estimate signal from a single nucleic acid probe, from a single antibody probe, a combination two or more nucleic acid probes, a combination of two or more antibody probes, and/or any combination of nucleic acid and antibody probes.

A digital pathology system 200 for imaging and analyzing specimens, in accordance with some embodiments, is illustrated in FIG. 1. The digital pathology system 200 may comprise an imaging apparatus 12 (e.g. an apparatus having means for scanning a specimen-bearing microscope slide) and a computer 14, whereby the imaging apparatus 12 and computer may be communicatively coupled together (e.g. directly, or indirectly over a network 20). The computer system 14 can include a desktop computer, a laptop computer, a tablet, or the like, digital electronic circuitry, firmware, hardware, memory, a computer storage medium, a computer program or set of instructions (e.g. where the program is stored within the memory or storage medium), one or more processors (including a programmed processor), and any other hardware, software, or firmware modules or combinations thereof. For example, the computing system 14 illustrated in FIG. 1 may comprise a computer with a display device 16 and an enclosure 18. The computer can store digital images in binary form (locally, such as in a memory, on a server, or another network connected device). The digital images can also be divided into a matrix of pixels. The pixels can include a digital value of one or more bits, defined by the bit depth. The skilled artisan will appreciate that other computer devices or systems may be utilized and that the computer systems described herein may be communicatively coupled to additional components, e.g. specimen analyzers, microscopes, other imaging systems, automated slide preparation equipment, etc. Some of these additional components and the various computers, networks, etc. that may be utilized are described further herein.

In general, the imaging apparatus 12 (or other image source including pre-scanned images stored in a memory) can include, without limitation, one or more image capture devices. Image capture devices can include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. An image sensor, for example, a CCD sensor can capture a digital image of the specimen. In some embodiments, the imaging apparatus 12 is a brightfield imaging system, a multispectral imaging (MSI) system or a fluorescent microscopy system. The digitized tissue data may be generated, for example, by an image scanning system, such as a VENTANA DP200 scanner or a VENTANA iScan HT scanner by VENTANA MEDICAL SYSTEMS, Inc. (Tucson, Ariz.) or other suitable imaging equipment. Additional imaging devices and systems are described further herein. The skilled artisan will appreciate that the digital color image acquired by the imaging apparatus 12 can be conventionally composed of elementary color pixels. Each colored pixel can be coded over three digital components, each comprising the same number of bits, each component corresponding to a primary color, generally red, green or blue, also denoted by the term "RGB" components.

Figure 2:
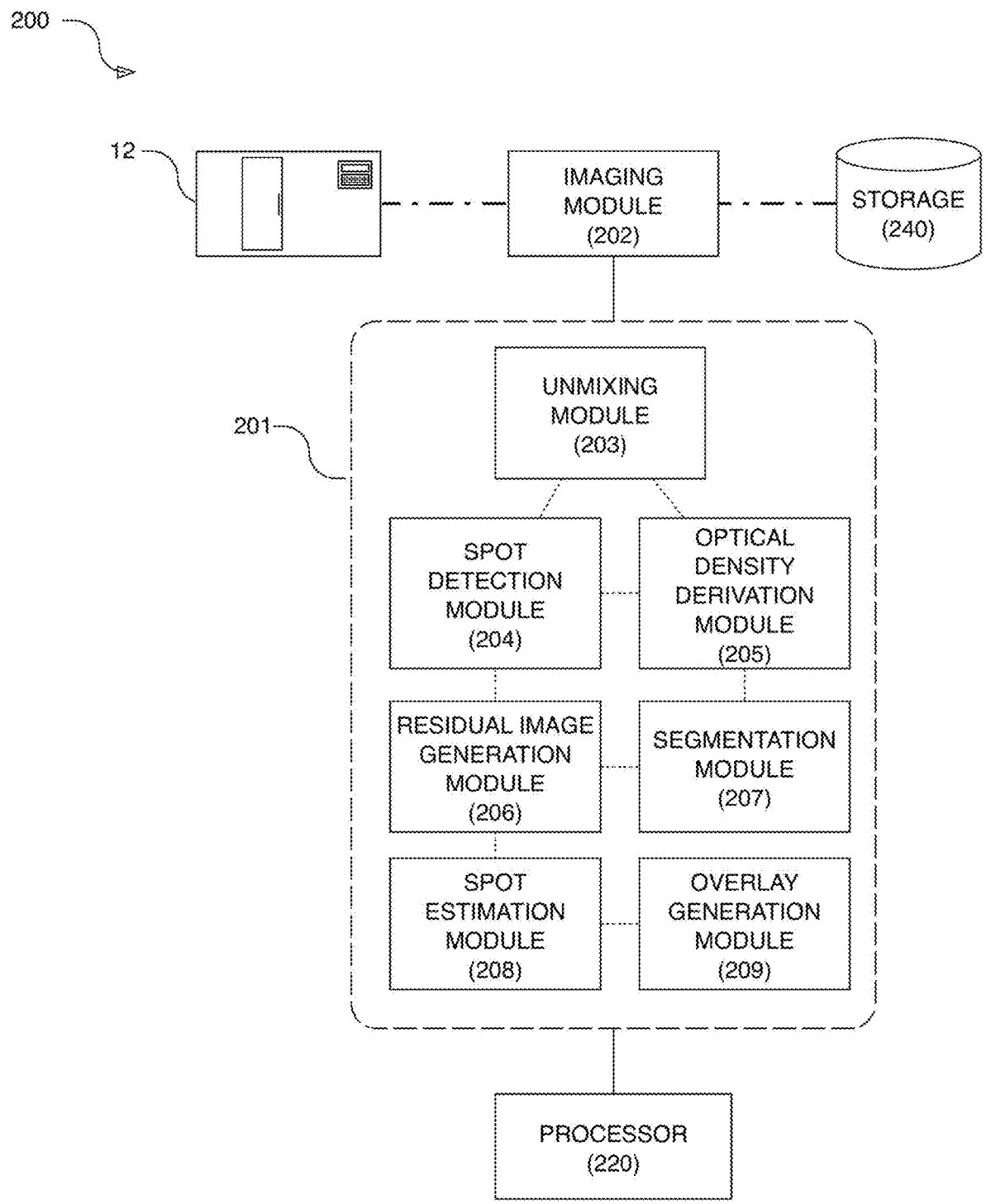
FIG. 2 sets forth various modules that can be utilized in a digital pathology system or within a digital pathology workflow, in accordance with some embodiments.

FIG. 2 provides an overview of the various modules utilized within the presently disclosed digital pathology system. In some embodiments, the digital pathology system employs a computer device 200 or computer-implemented method having one or more processors 220 and at least one memory 201, the at least one memory 201 storing non-transitory computer-readable instructions for execution by the one or more processors to cause the one or more processors 220 to execute instructions (or stored data) in one or more modules (e.g. modules 202 through 210).

Figure 3A:
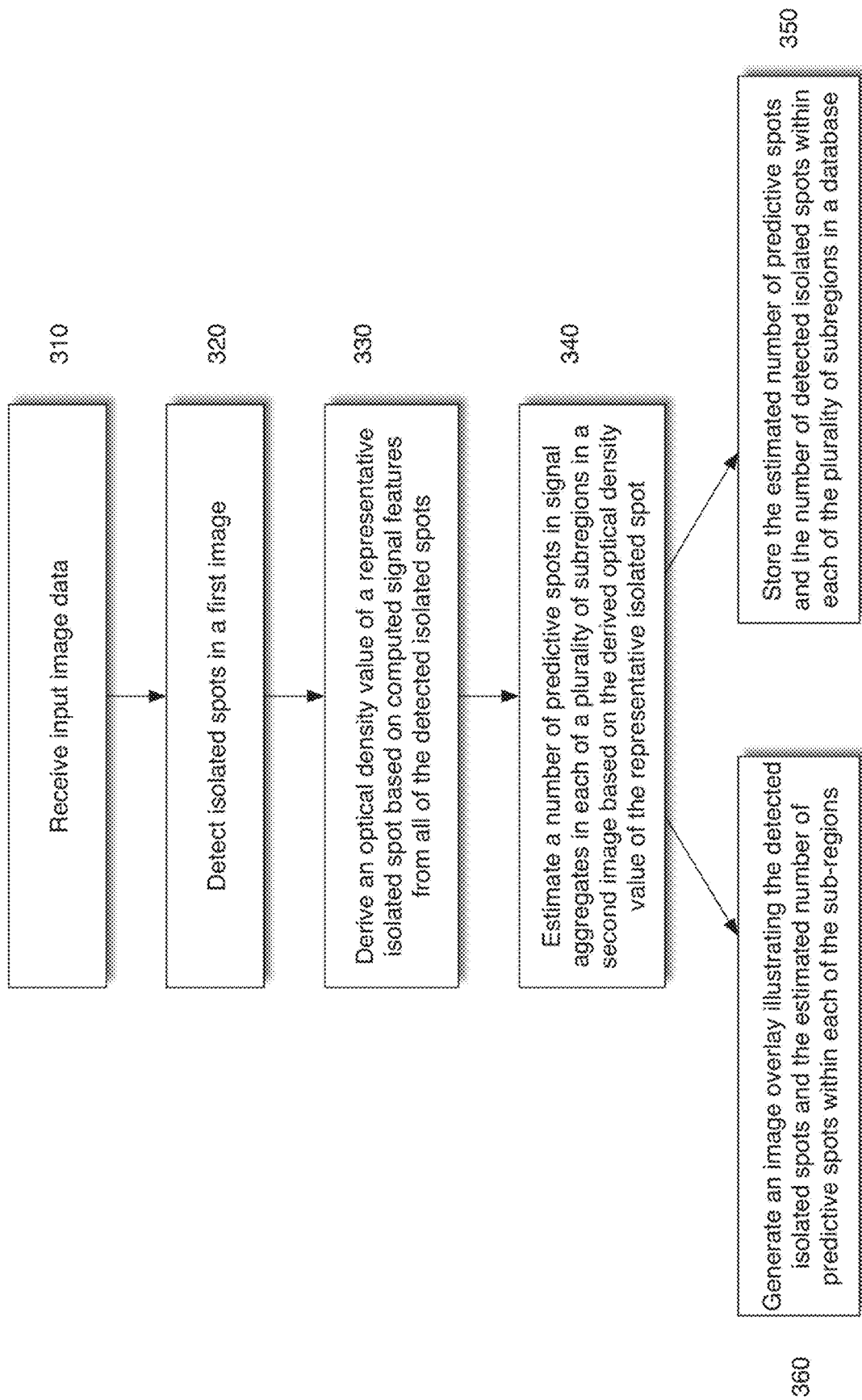
FIG. 3A sets forth a flowchart providing an overview of the steps for estimating a quantity of one or more signals corresponding to one or more biomarkers, respectively, in a whole slide image or any portion thereof, and further illustrates the optional steps of generating overlays or storing the computed data, in accordance with some embodiments.

With reference to FIGS. 2 and 3A, the present disclosure provides a computer-implemented system and method of estimating an amount of signal corresponding to at least one biomarker in an image of a biological sample. In some embodiments, the system may include: (a) an imaging module 202 which is adapted to generate image data of a stained biological sample (e.g. a sample stained for at least the presence of one or more protein biomarkers or one or more nucleic acid sequences, including one or more mRNA sequences) (step 310); (b) a spot detection module 204 adapted to detect isolated spots corresponding to a biomarker signal in an input image (step 320); (c) an optical density derivation module 205 configured to derive an optical density value of a typical isolated spot based on certain characteristics of all of the detected isolated spots (e.g. intensity, size, blurriness, roundness, etc. characteristics) (step 330); (d) a spot estimation module 208 adapted to estimate a number of predictive spots within spot or signal blob aggregates in each of a plurality of sub-regions based on computed spot characteristics (step 340); and (e) a database or other storage subsystem 240 to store the estimated number of predicted spots and the number of detected spots within each of the plurality of sub-regions in a database 240 (step 350).

Figure 3B:
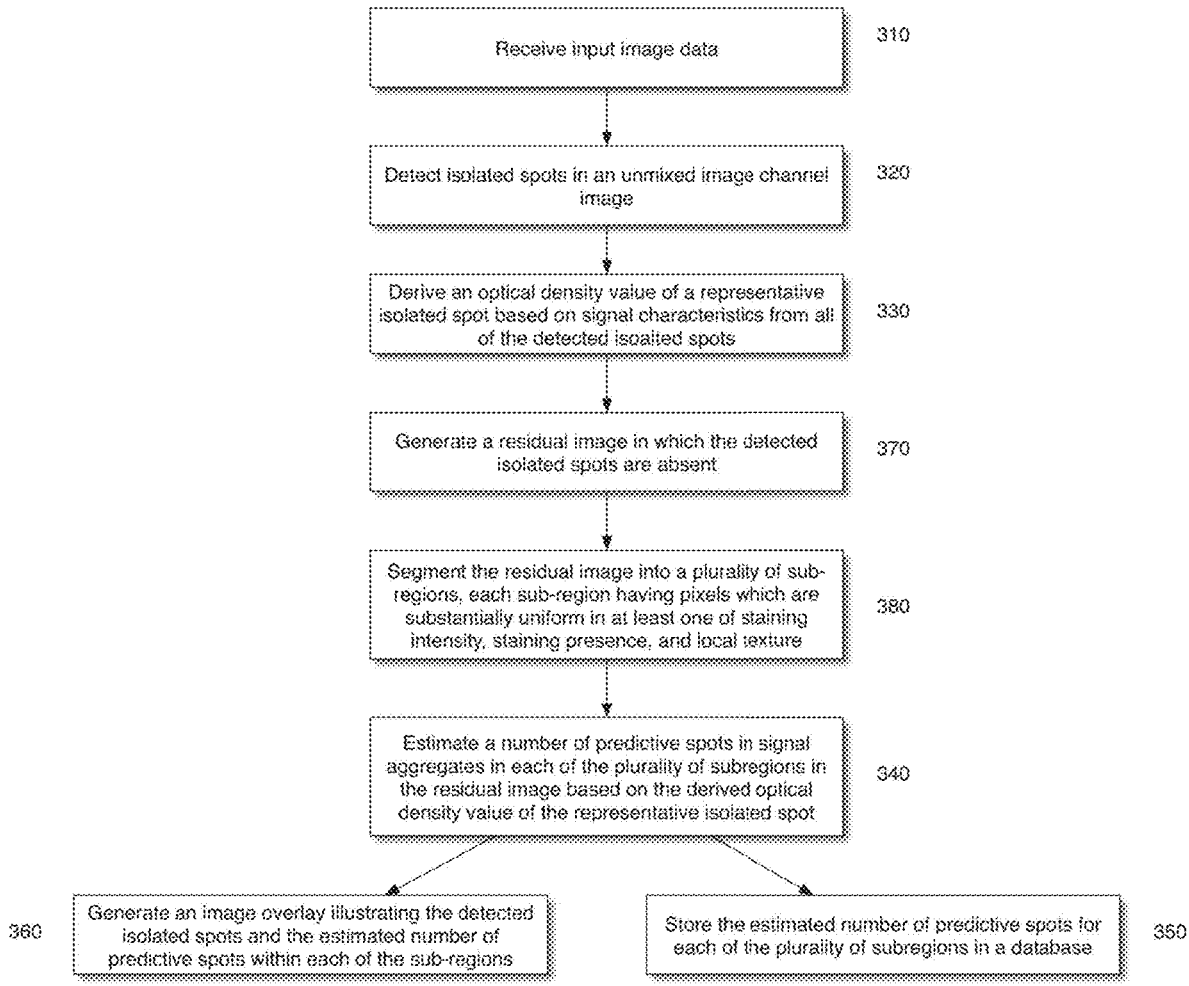
FIG. 3B sets forth a flowchart illustrating the steps for estimating a quantity of one or more signals corresponding to one or more biomarkers, respectively, in a whole slide image or any portion thereof, and further illustrates the optional steps of generating overlays or storing the computed data, in accordance with some embodiments.

The skilled artisan will also appreciate that additional modules may be incorporated into the workflow as needed. For example, and with reference to FIG. 3B, an unmixing module 203 may optionally be run to provide image channel images corresponding to a particular stain or biomarker (e.g. when a multiplex image is used as an input image). As such, after unmixing, the received input image is unmixed into an image having signal corresponding to a single biomarker, and this unmixed image channel image may be used for detecting isolated spots (step 320).

In some embodiments, the system includes a residual image generation module 206 which may be run to compute an image that is substantially free from the detected isolated spots (step 370). As such, an input image channel image may be processed such that the detected isolated spots from step 320 are removed, leaving only blobs of signal aggregates.

In other embodiments, a segmentation module 207 may be run to divide the input image (e.g. a residual image from step 370) into a series of sub-regions (step 380). The resultant segmented regions, in some embodiments, are substantially uniform in at least one of staining presence, staining intensity, or texture. In some embodiments, the segmented regions are each superpixels, as described herein.

In yet other embodiments, an overlay generation module 209 may be run such that a visual representation of the detected isolated spots and the estimated number of predictive spots in any signal aggregates may be superimposed over the input image (step 360).

Figure 3C:
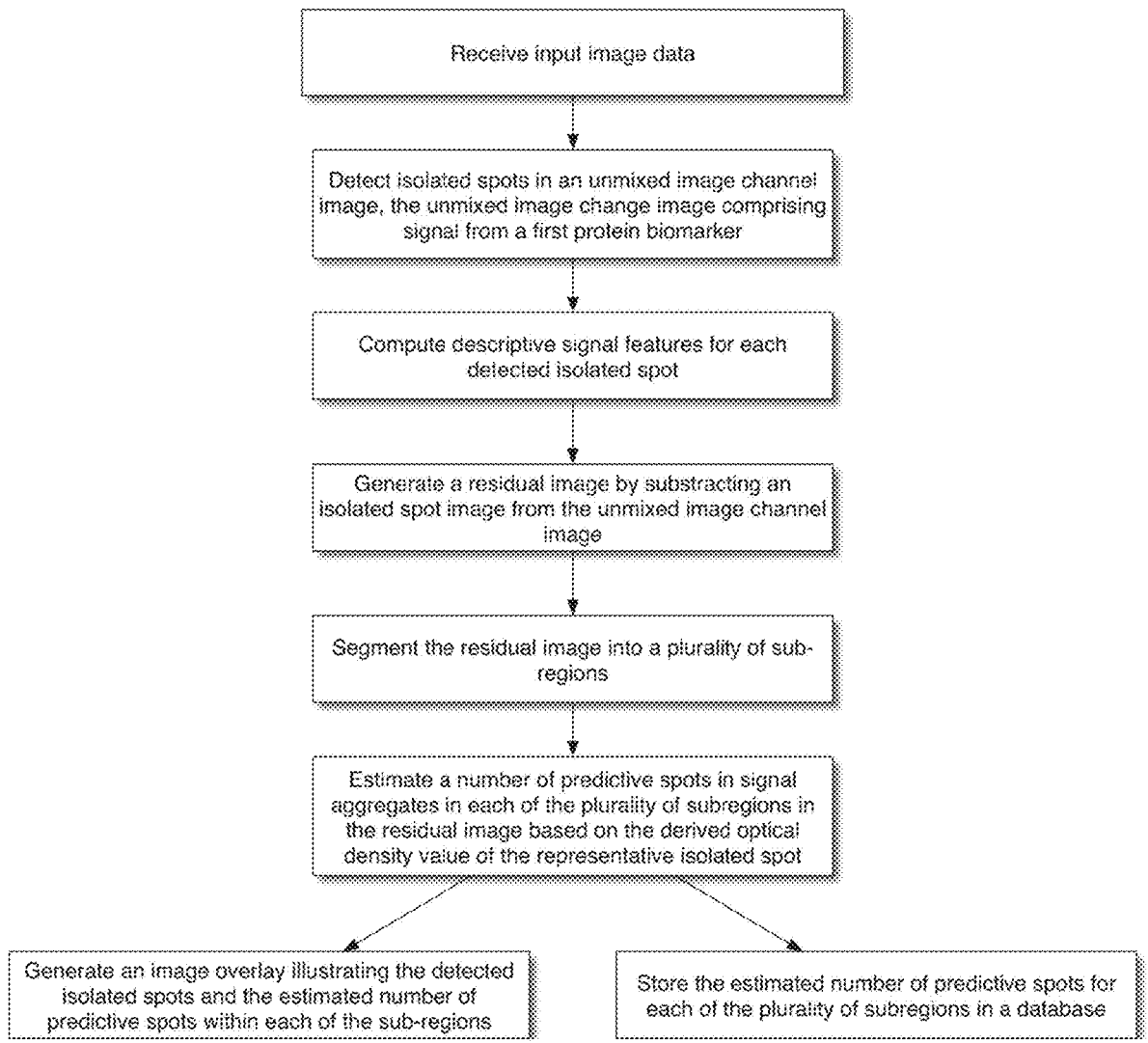
FIG. 3C sets forth a flowchart illustrating a non-limiting method for estimating a quantity of one or more signals corresponding to one or more protein biomarkers, in accordance with some embodiments.
Figure 3D:
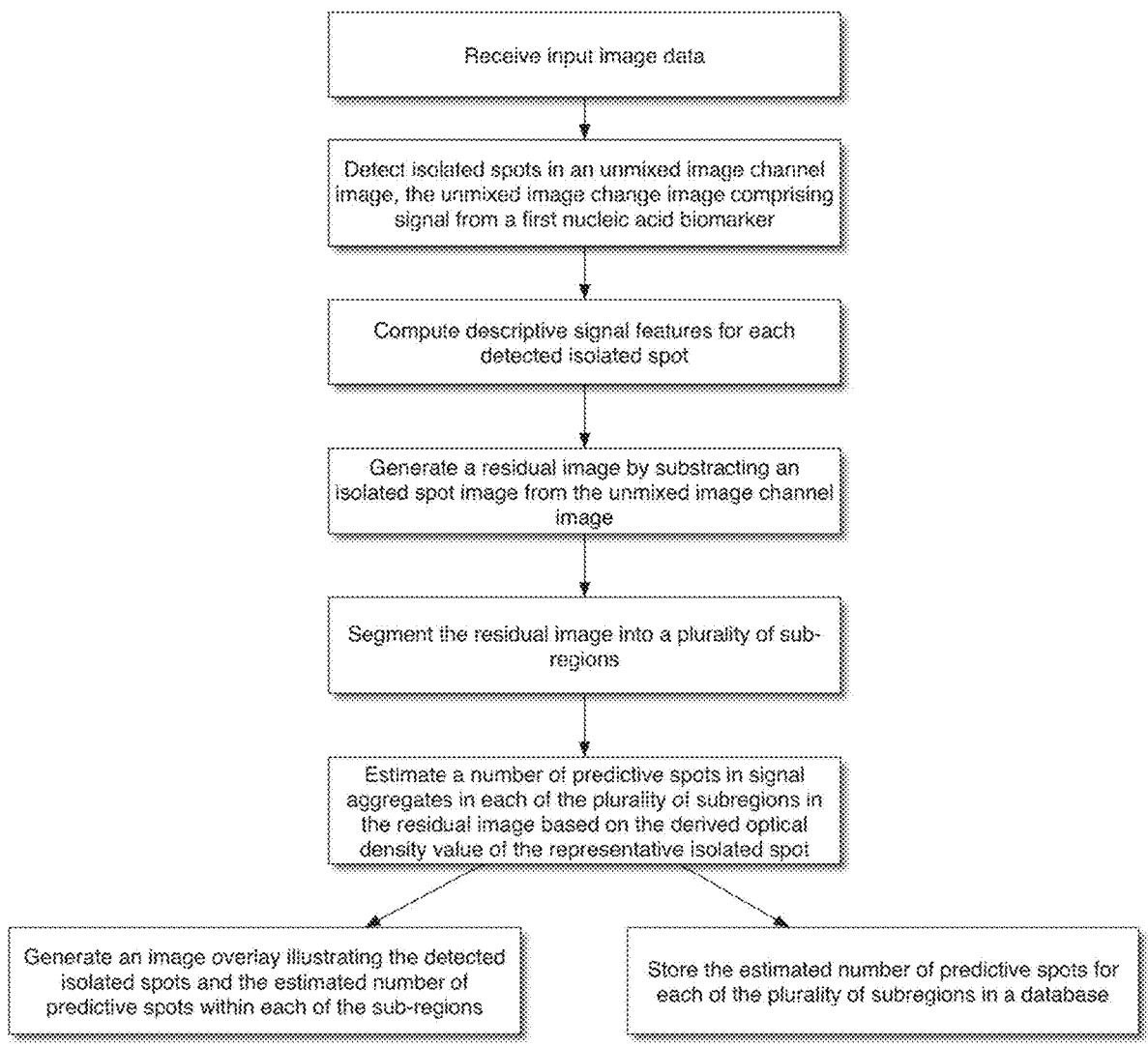
FIG. 3D sets forth a flowchart illustrating a non-limiting method for estimating a quantity of one or more signals corresponding to one or more nucleic acid biomarkers, in accordance with some embodiments.

The skilled artisan will also appreciate that the system may be adapted to utilize received input images of biological specimens stained in an in situ hybridization assay or an immunohistochemistry assay (or a combination of the two assays). For example, FIG. 3C illustrates the steps of estimating a quantity of a single protein biomarker. Of course, the steps illustrated in FIG. 3C may be repeated for a second protein biomarker, and the quantities of the first estimated protein biomarker and the second estimated protein biomarker may be compared and/or used for further downstream analysis. Likewise, FIG. 3D illustrates the steps of estimating a quantity of a single nucleic acid biomarker. Of course, the steps illustrated in FIG. 3D may be repeated with a second nucleic acid biomarker, and the quantities of the first estimated nucleic acid biomarker and the second estimated nucleic acid biomarker may be compared and/or used for further downstream analysis.

Figure 3E:
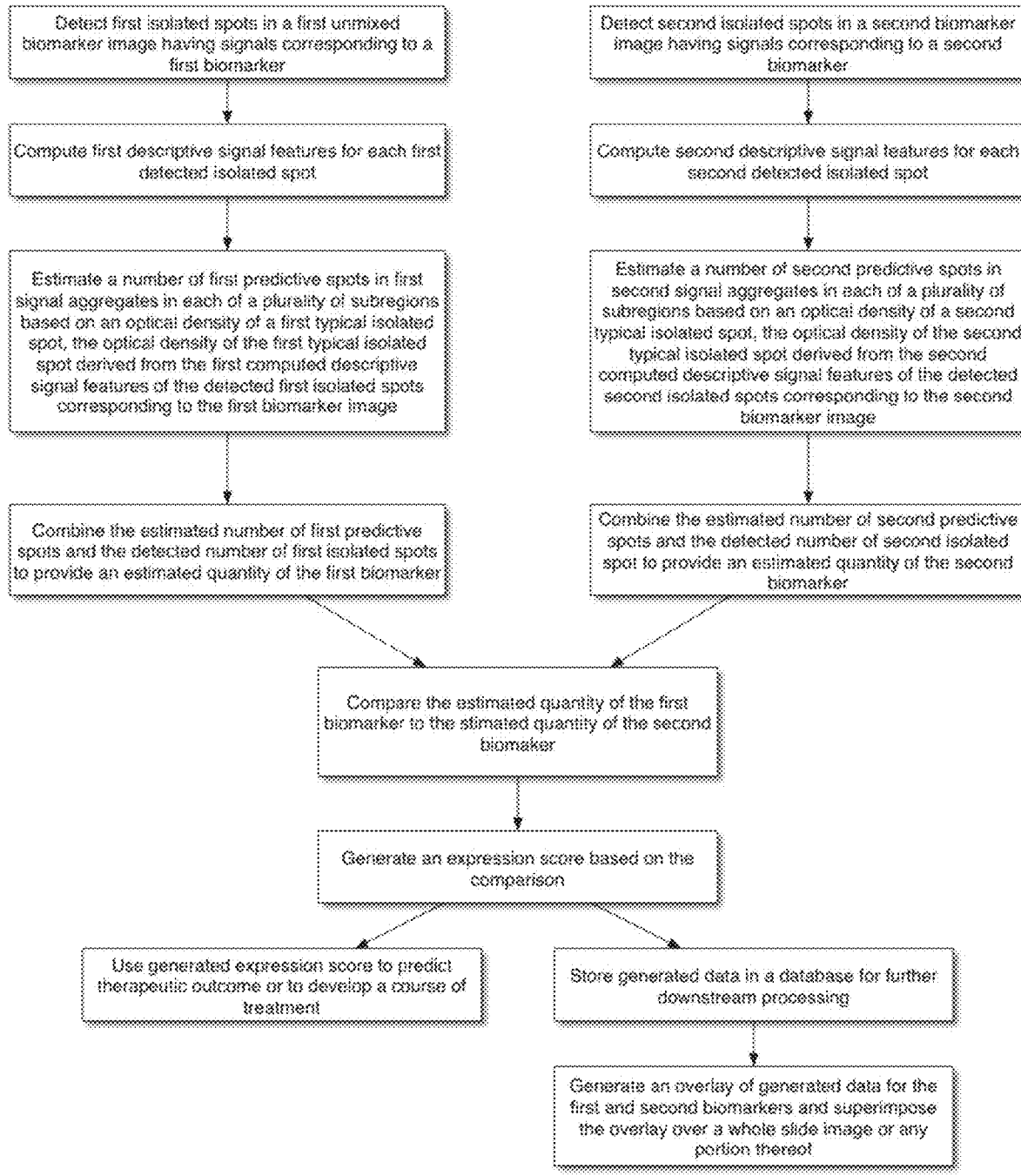
FIG. 3E sets forth a flowchart illustrating a non-limiting method for estimating the quantities of at least two signals corresponding to at least two biomarkers in a whole slide image or any portion thereof, in accordance with some embodiments.

Moreover, any of the modules identified in FIG. 2 may be run more than once. For example, modules 204 through 208 may be run a first time to quantify signals from a first biomarker (e.g. signals corresponding to a first mRNA probe), and modules 204 through 208 may be run a second time to quantify signals from a second biomarker (e.g. signals corresponding to a second mRNA probe). For example, the unmixing module may be used to unmix a received image (step 310) having at least two stains corresponding to different biomarkers into at least two respective image channel images. Modules 204 through 208 may be run a first time on a first image channel image to provide an estimate of the predictive spots (corresponding to a first biomarker) in each of a plurality of sub-regions. Modules 204 through 208 may then be run a second time on a second image channel image to provide an estimate of predictive spots (corresponding to a second biomarker), again in each of a plurality of sub-regions. The results may then be combined such that that an estimated number of predictive spots for each biomarker may be derived and such that comparisons between a quantity of first biomarker and second biomarker may be made (e.g. to provide a prognosis or to develop a course of treatment). These and other steps for comparing the results of the estimation of the quantity of two biomarkers is illustrated in FIG. 3E.

The skilled artisan will also appreciate that additional modules or databases not depicted in FIG. 2 may be incorporated into the workflow. For example, an image pre-processing module may be run to apply certain filters to the acquired images or to identify certain histological and/or morphological structures within the tissue samples. In addition, a region of interest selection module may be utilized to select a particular portion of an image for analysis.

Moreover, a module for removing chromatic aberrations present in an input image may be run. The chromatic aberration is the pronominal in the optical sensor that is an effect resulting from dispersion in which there is a failure of the lens to focus all colors to the same convergence point. This effect may occur when images are acquired using a mounted microscope camera. Therefore, the microscope images should be corrected to reduce this effect, which may have an impact on the spot count. In some embodiments, the correction is performed by simply shifting the pixels of red (R), green (G), and blue (B) channels, and it could reduce the rainbow effect present in the images. The chromatic aberration removal may be available as an internal module to correct this effect on the images acquired using a digital scanner.

Image Acquisition Module

In some embodiments, as an initial step, and with reference to FIG. 2, the digital pathology system 200 runs an imaging module 202 to capture images or image data (such as from a scanning device 12) of a biological sample having one or more stains (step 310). In some embodiments, the images received or acquired are RGB images or multispectral images (e.g. multiplex brightfield and/or dark field images). In some embodiments, the images captured are stored in memory 201.

The images or image data (used interchangeably herein) may be acquired using the scanning device 12, such as in real-time. In some embodiments, the images are acquired from a microscope or other instrument capable of capturing image data of a specimen-bearing microscope slide, as noted herein. In some embodiments, the images are acquired using a 2D scanner, such as one capable of scanning image tiles, or a line scanner capable of scanning the image in a line-by-line manner, such as the VENTANA DP 200 scanner. Alternatively, the images may be images that have been previously acquired (e.g. scanned) and stored in a memory 201 (or, for that matter, retrieved from a server via network 20).

In some embodiments, the images received as input are whole slide images. In other embodiments, the images received as input are portions of a whole slide image. In some embodiments, a whole slide image is broken down into several portions, e.g. tiles, and each portion or tile may be independently analyzed (e.g. using the modules set forth in FIG. 2 and the methods illustrated in at least FIGS. 3A and 3B). After the portions or tiles are independently analyzed (e.g. providing an estimation of signal quantity per sub-region per tile), the data from each portion or tile may be stored independently (step 350) and/or reported (step 360) at the whole slide level (see also FIG. 15).

The biological sample may be stained through application of one or more stains, and the resulting image or image data comprises signals corresponding to each of the one or more stains. In some embodiments, the input images are simplex images having only a single stain (e.g., stained with 3,3'-diaminobenzidine (DAB), silver (Ag+) stain). In some embodiments, the biological sample may be stained in a multiplex assay for two or more stains (thus providing multiplex images) (e.g., Ag+ for KAPPA mRNA sequences and sulforhodamine B (SRB) for LAMBDA mRNA sequences). In some embodiments, the biological samples are stained for at least two biomarkers. In other embodiments, the biological samples are stained for the presence of at least two biomarkers and also stained with a primary stain (e.g. hematoxylin).

In some embodiments, the biological samples are stained in an immunohistochemistry assay for the presence of one or more protein biomarkers. For example, the biological sample may be stained for the presence of a human epidermal growth factor receptor 2 protein (HER2 protein).

In other embodiments, the biological samples are stained in an in situ hybridization (ISH) assay for the presence of one or more nucleic acids, including mRNA. U.S. Pat. No. 7,087,379 (the disclosure of which is hereby incorporated by reference herein in its entirety) describes methods of staining samples with ISH probes such that individual spots, representing single copies, may be observed and detected. In some embodiments, several target genes are simultaneously analyzed by exposing a cell or tissue sample to a plurality of nucleic acid probes that have been labeled with a plurality of different nucleic acid tags. For example, a plurality of nucleic acid probes can be labeled with a plurality of chromogenic and/or fluorescent compounds having different emission wavelengths, thereby permitting simultaneous multicolored analysis to be performed in a single step on a single target cell or tissue sample.

For example, the INFORM HER2 Dual ISH DNA Probe Cocktail Assay from Ventana Medical Systems, Inc., is intended to determine HER2 gene status by enumeration of the ratio of the HER2 gene to Chromosome 17. The HER2 and Chromosome 17 probes are detected using two-color chromogenic in situ hybridization on formalin-fixed, paraffin-embedded tissue samples, such as human breast cancer tissue specimens or human gastric cancer tissue specimens. For the HER2 Dual ISH assay, the signals are silver signals ("black signals") and red signals, corresponding to black dots and red dots, respectively, in an input image. For the HER2 Dual ISH assay, cell based scoring involves counting of red and black dots inside selected cells, where the HER2 gene expression is expressed through black dots and Chromosome-17 is expressed through red dots.

By way of another example, the biological samples may be stained in an ISH assay with a plurality of mRNA probes. Detection of B cell clonality is useful for assisting in the diagnosis of B cell lymphomas and the clonality assessment can be accomplished through evaluation of KAPPA and LAMBDA light chain expression. As such, a cocktail of KAPPA oligoprobes and a cocktail of LAMBDA oligoprobes may be introduced to a sample to facilitate multiplex detection of KAPPA and LAMBDA mRNA. As noted herein, KAPPA mRNA may be detected with silver (Ag) (appears as a black color) and LAMBDA mRNA may be detected with Tyramide SRB (appears as a purple color). By analyzing a ratio of an amount of detected KAPPA mRNA and detected LAMBDA mRNA, a determination may be made as to whether a sample is non-lymphoma, lymphoma (KAPPA restricted), or lymphoma (LAMBDA restricted). U.S. Pat. No. 8,236,502 describes specific KAPPA and LAMBDA mRNA probes which may be employed as well as their method of detection, the disclosure of which is hereby incorporated by reference herein in its entirety.

Chromogenic stains may comprise Hematoxylin, Eosin, Fast Red, or 3,3'-Diaminobenzidine (DAB). In some embodiments, the tissue sample is stained with a primary stain (e.g. hematoxylin). In some embodiments, the tissue sample is also stained with a secondary stain (e.g. eosin). In some embodiments, the tissue sample is stained in an IHC assay for a particular biomarker. Of course, the skilled artisan will appreciate that any biological sample may also be stained with one or more fluorophores.

A typical biological sample is processed in an automated staining/assay platform that applies a stain to the sample. There are a variety of commercial products on the market suitable for use as the staining/assay platform, one example being the Discovery™ product of Ventana Medical Systems, Inc. (Tucson, Ariz.). The camera platform may also include a bright field microscope, such as the VENTANA iScan HT or the VENTANA DP 200 scanners of Ventana Medical Systems, Inc., or any microscope having one or more objective lenses and a digital imager. Other techniques for capturing images at different wavelengths may be used. Further camera platforms suitable for imaging stained biological specimens are known in the art and commercially available from companies such as Zeiss, Canon, Applied Spectral Imaging, and others, and such platforms are readily adaptable for use in the system, methods and apparatus of this subject disclosure.

In some embodiments, the input images are masked such that only tissue regions are present in the images. In some embodiments, a tissue region mask is generated to mask non-tissue regions from tissue regions. In some embodiments, a tissue region mask may be created by identifying the tissue regions and automatically or semi-automatically (i.e., with minimal user input) excluding the background regions (e.g. regions of a whole slide image corresponding to glass with no sample, such as where there exists only white light from the imaging source). The skilled artisan will appreciate that in addition to masking non-tissue regions from tissue regions, the tissue masking module may also mask other areas of interest as needed, such as a portion of a tissue identified as belonging to a certain tissue type or belonging to a suspected tumor region. In some embodiments, a segmentation technique is used to generate the tissue region masked images by masking tissue regions from non-tissue regions in the input images. Suitable segmentation techniques are as such known from the prior art, (cf. Digital Image Processing, Third Edition, Rafael C. Gonzalez, Richard E. Woods, chapter 10, page 689 and Handbook of Medical Imaging, Processing and Analysis, Isaac N. Bankman Academic Press, 2000, chapter 2). In some embodiments, an image segmentation technique is utilized to distinguish between the digitized tissue data and the slide in the image, the tissue corresponding to the foreground and the slide corresponding to the background. In some embodiments, the component computes the Area of Interest (AOI) in a whole slide image in order to detect all tissue regions in the AOI while limiting the amount of background non-tissue area that is analyzed. A wide range of image segmentation techniques (e.g., HSV color-based image segmentation, Lab image segmentation, mean-shift color image segmentation, region growing, level set methods, fast marching methods, etc.) can be used to determine, for example, boundaries of the tissue data and non-tissue or background data. Based at least in part on the segmentation, the component can also generate a tissue foreground mask that can be used to identify those portions of the digitized slide data that correspond to the tissue data. Alternatively, the component can generate a background mask used to identify those portions of the digitized slide date that do not correspond to the tissue data.

This identification may be enabled by image analysis operations such as edge detection, etc. A tissue region mask may be used to remove the non-tissue background noise in the image, for example the non-tissue regions. In some embodiments, the generation of the tissue region mask comprises one or more of the following operations (but not limited to the following operations): computing the luminance of the low resolution analysis input image, producing a luminance image, applying a standard deviation filter to the luminance image, producing a filtered luminance image, and applying a threshold to filtered luminance image, such that pixels with a luminance above a given threshold are set to one, and pixels below the threshold are set to zero, producing the tissue region mask. Additional information and examples relating to the generation of tissue region masks is disclosed in US Publication No. 2017/0154420, entitled "An Image Processing Method and System for Analyzing a Multi-Channel Image Obtained from a Biological Tissue Sample Being Stained by Multiple Stains," the disclosure of which is hereby incorporated by reference herein in its entirety.

In some embodiments, a region of interest identification module may be used to select a portion of the biological sample for which image data should be acquired, e.g. a region of interest having a large concentration of lymphocytes cells or a region suspected of having a large concentration of lymphocytes. Methods of determining a region of interest are described in US Publication No. 2017/0154420, the disclosure of which is hereby incorporated by reference herein in its entirety. In general, the US Publication No. 2017/0154420 discloses: an image processing method for analyzing a multi-channel image obtained from a biological tissue sample being stained by multiple stains, the method comprising: a. unmixing the multi-channel image to provide one unmixed image per channel, b. spatial low pass filtering of at least one of the unmixed images, c. local maximum filtering of the at least one of the spatial low pass filtered unmixed images, d. thresholding the at least one of the spatial low pass filtered unmixed images to identify at least one set of neighboring pixels, and e. defining a region of interest by extracting an image portion of the multi-channel image from an image location given by the set of neighboring pixels, the region of interest having a predetermined size and shape.

Unmixing Module

In some embodiments, the images received as input may be multiplex images, i.e. the image received is of a biological sample stained with more than one stain (e.g. an image stained for the presence of the KAPPA mRNA and LAMBDA mRNA probes; or for the HER2 and Chromosome 17 probes). In these embodiments, and prior to further processing, the multiple image is first unmixed into its constituent channels, such as with an unmixing module 203, where each unmixed channel corresponds to a particular stain or signal.

In some embodiments, in a sample comprising one or more stains, individual images may be produced for each channel of the one or more stains. The skilled artisan will appreciate that features extracted from these channels are useful in describing the different biological structures present within any image of a tissue (e.g. nuclei, membranes, cytoplasm, nucleic acids, etc.). For example, and in the context of the KAPPA mRNA and LAMBA mRNA probes described herein, unmixing would result in a first unmixed image channel image having silver (or black) signals, a second unmixed image channel image having purple signals, and a third unmixed image channel having hematoxylin signals. Such unmixing results, again in the context of the KAPPA mRNA and LAMBA mRNA probes, are illustrated in FIGS. 6A to 6C, 7A to 7C, and 8A to 8D. In some embodiments, the unmixed images (often referred to as "channel images" or "image channel images") and may be used as the input for each module described herein. In some embodiments, the channel having the strongest color is unmixed first. For example, a silver/black channel may be unmixed prior to a purple channel.

The multi-spectral image provided by the imaging module 202 is a weighted mixture of the underlying spectral signals associated the individual biomarkers and noise components. At any particular pixel, the mixing weights are proportional to the biomarker expressions of the underlying co-localized biomarkers at the particular location in the tissue and the background noise at that location. Thus, the mixing weights vary from pixel to pixel. The spectral unmixing methods disclosed herein decompose the multi-channel pixel value vector at each and every pixel into a collection of constituent biomarker end members or components and estimate the proportions of the individual constituent stains for each of the biomarkers.

Unmixing is the procedure by which the measured spectrum of a mixed pixel is decomposed into a collection of constituent spectra, or endmembers, and a set of corresponding fractions, or abundances, that indicate the proportion of each endmember present in the pixel. Specifically, the unmixing process can extract stain-specific channels to determine local concentrations of individual stains using reference spectra that are well known for standard types of tissue and stain combinations. The unmixing may use reference spectra retrieved from a control image or estimated from the image under observation. Unmixing the component signals of each input pixel enables retrieval and analysis of stain-specific channels, such as a hematoxylin channel and an eosin channel in H&E images, or a diaminobenzidine (DAB) channel and a counterstain (e.g., hematoxylin) channel in IHC images. The terms "unmixing" and "color deconvolution" (or "deconvolution") or the like (e.g. "deconvolving," "unmixed") are used interchangeably in the art.

In some embodiments, the multiplex images are unmixed with unmixing module 205 using liner unmixing. Linear unmixing is described, for example, in 'Zimmermann "Spectral Imaging and Linear Unmixing in Light Microscopy" Adv Biochem Engin/Biotechnology (2005) 95:245-265' and in in C. L. Lawson and R. J. Hanson, "Solving least squares Problems," PrenticeHall, 1974, Chapter 23, p. 161,' the disclosures of which are incorporated herein by reference in their entirety. In linear stain unmixing, the measured spectrum ($S(\lambda)$) at any pixel is considered a linear mixture of stain spectral components and equals the sum of the proportions or weights (A) of each individual stain's color reference ($R(\lambda)$) that is being expressed at the pixel $$S(\lambda) = A_1 \cdot R_1(\lambda) + A_2 \cdot R_2(\lambda) + A_3 \cdot R_3(\lambda) \ldots\ldots A_i ry(\lambda)$$

which can be more generally expressed as in matrix form as $$S(\lambda) = \sum A_i ry(\lambda) \text{ or } S = R \cdot A$$

If there are M channels images acquired and N individual stains, the columns of the M×N matrix R are the optimal color system as derived herein, the N×1 vector A is the unknown of the proportions of individual stains and the M×1 vector S is the measured multichannel spectral vector at a pixel. In these equations, the signal in each pixel (S) is measured during acquisition of the multiplex image and the reference spectra, i.e. the optimal color system, is derived as described herein. The contributions of various stains (Ai) can be determined by calculating their contribution to each point in the measured spectrum. In some embodiments, the solution is obtained using an inverse least squares fitting approach that minimizes the square difference between the measured and calculated spectra by solving the following set of equations, $$\left[\partial \sum_j \{S(\lambda_j) - \sum_i A_i ry(\lambda_j)\}2\right] / \partial A_i = 0$$

In this equation, j represents the number of detection channels and i equals the number of stains. The linear equation solution often involves allowing a constrained unmixing to force the weights (A) to sum to unity.

In other embodiments, unmixing is accomplished using the methods described in WO2014/195193, entitled "Image Adaptive Physiologically Plausible Color Separation," filed on May 28, 2014, the disclosure of which is hereby incorporated by reference in its entirety herein. In general, WO2014/195193 describes a method of unmixing by separating component signals of the input image using iteratively optimized reference vectors. In some embodiments, image data from an assay is correlated with expected or ideal results specific to the characteristics of the assay to determine a quality metric. In the case of low quality images or poor correlations against ideal results, one or more reference column vectors in matrix R are adjusted, and the unmixing is repeated iteratively using adjusted reference vectors, until the correlation shows a good quality image that matches physiological and anatomical requirements. The anatomical, physiological, and assay information may be used to define rules that are applied to the measured image data to determine the quality metric. This information includes how the tissue was stained, what structures within the tissue were intended or not intended to be stained, and relationships between structures, stains, and markers specific to the assay being processed. An iterative process results in stain-specific vectors that can generate images that accurately identify structures of interest and biologically relevant information, are free from any noisy or unwanted spectra, and therefore fit for analysis. The reference vectors are adjusted to within a search space. The search space defines a range of values that a reference vector can take to represent a stain. The search space may be determined by scanning a variety of representative training assays including known or commonly occurring problems and determining high-quality sets of reference vectors for the training assays.

In other embodiments, unmixing is accomplished using the methods described in WO2015/124772, entitled "Group Sparsity Model for Image Unmixing," filed on Feb. 23, 215, the disclosure of which is hereby incorporated by reference in its entirety herein. In general, WO2015/124772 describes unmixing using a group sparsity framework, in which fractions of stain contributions from a plurality of colocation markers are modeled within a "same group" and fractions of stain contributions from a plurality of non-colocation markers are modeled in different groups, providing co-localization information of the plurality of colocation markers to the modeled group sparsity framework, solving the modeled framework using a group lasso to yield a least squares solution within each group, wherein the least squares solution corresponds to the unmixing of the colocation markers, and yielding a sparse solution among the groups that corresponds to the unmixing of the non-colocation markers. Moreover, WO2015124772 describes a method of unmixing by inputting image data obtained from the biological tissue sample, reading reference data from an electronic memory, the reference data being descriptive of the stain color of each one of the multiple stains, reading colocation data from electronic memory, the colocation data being descriptive of groups of the stains, each group comprising stains that can be collocated in the biological tissue sample, and each group forming a group for the group lasso criterion, at least one of the groups having a size of two or above, and calculating a solution of the group lasso criterion for obtaining the unmixed image using the reference data as a reference matrix. In some embodiments, the method for unmixing an image may comprise generating a group sparsity model wherein a fraction of a stain contribution from colocalized markers is assigned within a single group and a fraction of a stain contribution from non-colocalized markers is assigned within separate groups and solving the group sparsity model using an unmixing algorithm to yield a least squares solution within each group.

Spot and Blob Detection Module

Following image acquisition and/or unmixing, an image having a single biomarker channel is provided to the spot detection module 204 such that isolated spots within the image may be detected (as opposed to the "blobs" or signal aggregates). In other embodiments, an unmixed image channel image is used for input for the spot and blob detection module.

In some embodiments, a morphological operation is performed to detect isolated spots, i.e. dots, within the image. Based on mathematical morphology theory, binary morphological filtering is a technique for processing the images with a certain structure element having a pre-defined shape (e.g. a circle). The morphological filtering operation performs image filtering by examining the geometrical and topological structures of objects with the pre-defined shape. The basic idea is to probe an image with a simple, predefined shape, where the algorithm draws conclusions on how this shape fits or misses the shapes within the image. In some embodiments, a morphological operation is performed using a disk shaped structural element. In some embodiments, the radius of the disk-shaped element ranges from about 1 to about 2. In other embodiments, the radius of the disk-shaped element is 1. In some embodiments, Gaussian filtering/smoothing is performed prior to the detection. In some embodiments, a scaling parameter of 1 may be used.

Other methods of detecting isolated spots within an image are described in United States Patent Publication Nos. 2014/0377753 and 2017/0323148, the disclosures of which are hereby incorporated by reference herein in their entireties.

In some embodiments, following the detection of each of the isolated spots in the input image, the detected isolated spots are separated from the blobs in the input image, providing an "isolated spots image channel" and an "blob image channel." In some embodiments, the detected spots are "masked out" from a blob image channel. In some embodiments, the input image is assumed to contain objects with higher image values a background with low or nearly zero values. In some embodiments, and prior to "masking out," a smoothing operation is performed with a smooth border of 4 pixels width and with a morphological operation having a disk parameter of 2. From the "isolated spots image channel," the location of each of the detected isolated spots in the image may be ascertained, i.e. the Cartesian coordinates are found for each of the detected isolated spots. For example, the x,y coordinates may be found by determining the seed center of each detected isolated spot. For example, a seed center may be calculated by determining a centroid or center of mass of each detected isolated spot.

In some embodiments, small objects or blurred point sources may be detected using a multiscale Difference of Gaussians (DoG) approach. In general, difference of Gaussians is a feature enhancement algorithm that involves the subtraction of one blurred version of an original image from another, less blurred version of the original. In the simple case of grayscale images, the blurred images are obtained by convolving the original grayscale images with Gaussian kernels having differing standard deviations. It is believed that blurring an image using a Gaussian kernel suppresses only high-frequency spatial information. Subtracting one image from the other preserves spatial information that lies between the range of frequencies that are preserved in the two blurred images. Thus, the difference of Gaussians is a band-pass filter that discards all but a handful of spatial frequencies that are present in the original grayscale image. In some embodiments, spots of different sizes are detected using a DoG filter approach. In some embodiments, multiple spot sizes are configured in ascending order (small to large), but the processing is in the order large to small spots. In each iteration, a DoG filter is created from the given inner and outer filter sizes. The input or a residual image is filtered with this DoG filter, and an adaptive threshold decision is used to identify positive detections after a local non-maximum suppression. The respective detections are collected in a resulting seed/annotation object.

Figure 9A:
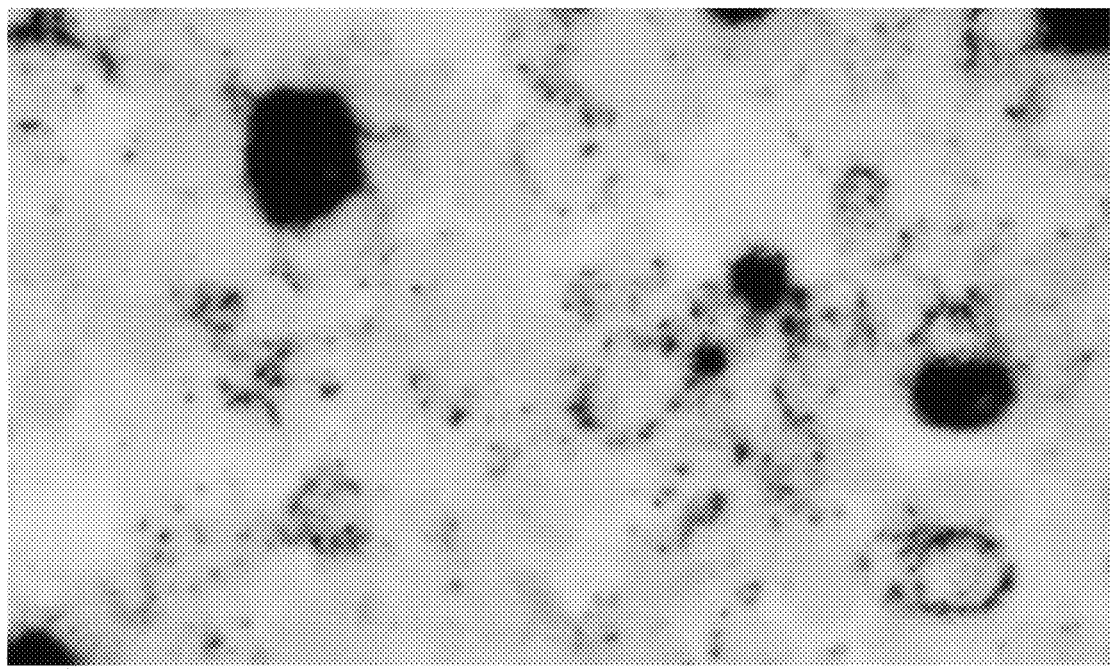
FIG. 9A provides an example of a portion of a whole slide image stained in an in situ hybridization assay.
Figure 9B:
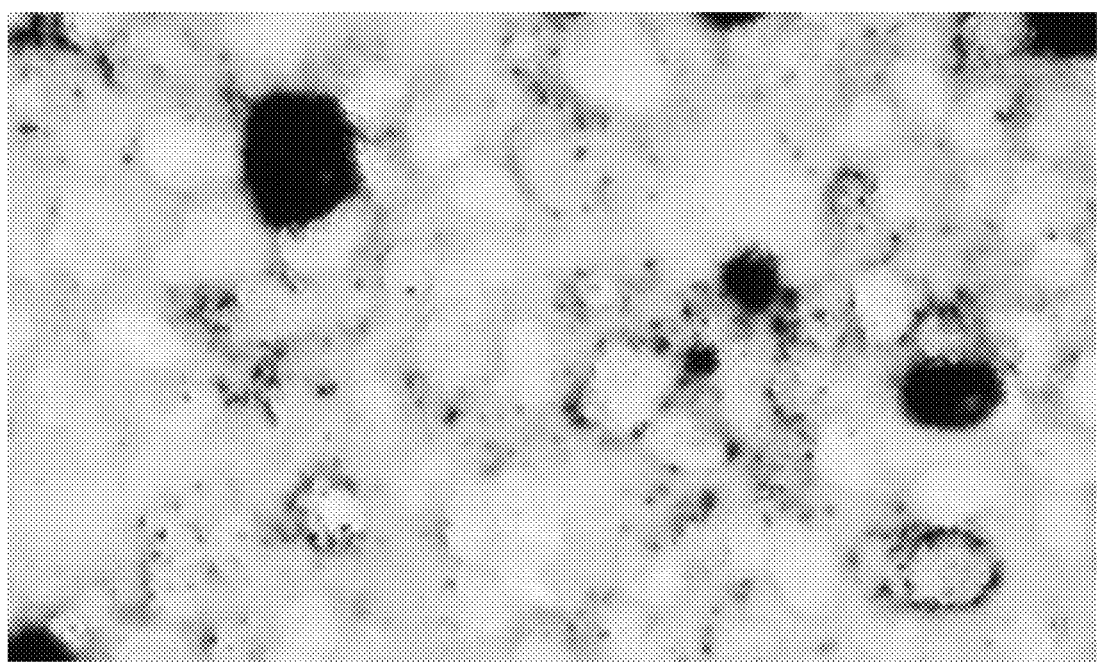
FIG. 9B illustrates the result of the unmixing of FIG. 9A into a single channel (silver/black channel).
Figure 9C:
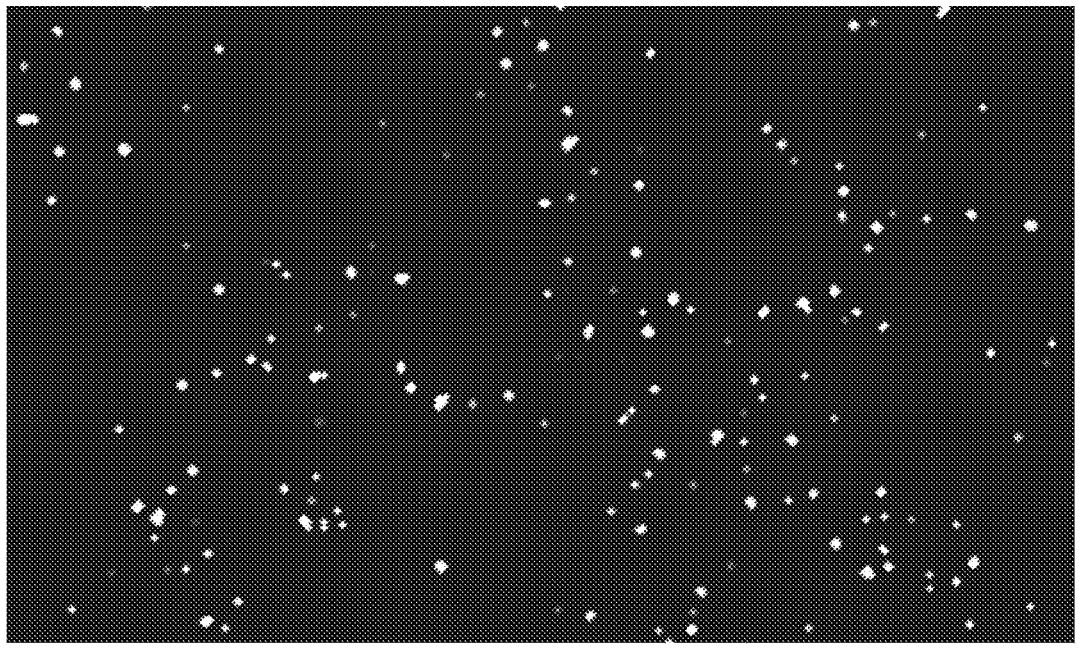
FIG. 9C illustrates the result of dot detection (a spot channel image) on the unmixed image channel image of FIG. 9B.
Figure 9D:
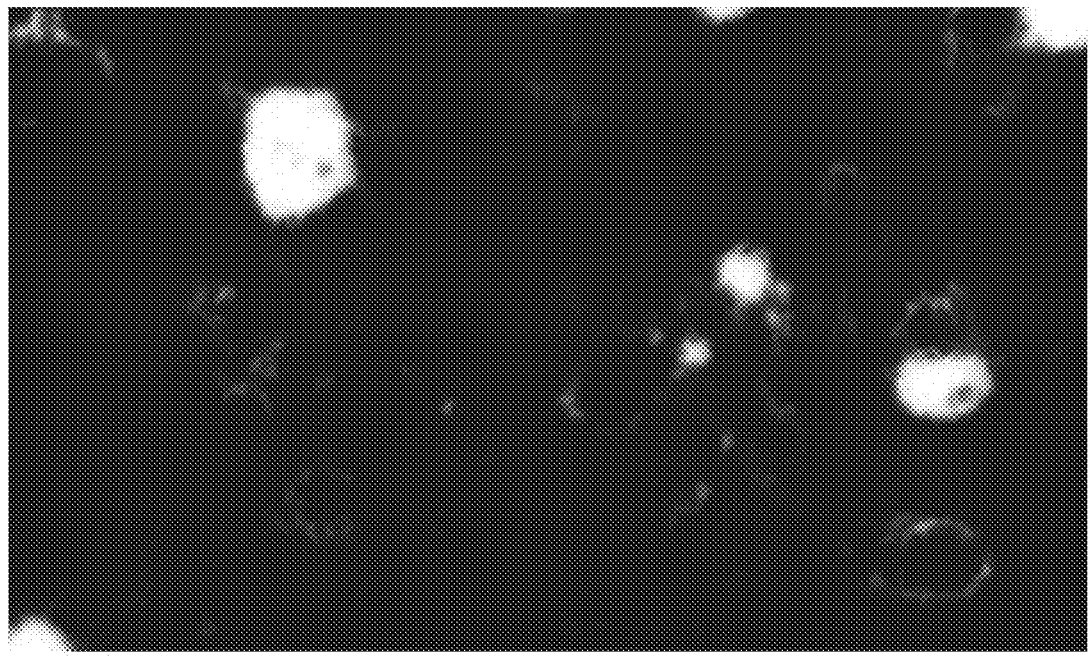
FIG. 9D illustrates a blob channel image whereby the signals from the detected isolated spots from FIG. 9C are substantially removed (e.g. subtracted out).
Figure 9E:
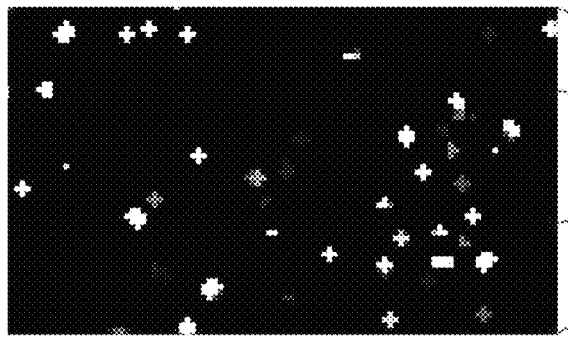
FIGS. 9E and 9F illustrate derived x,y locations of the detected isolated spots in the spot channel image of FIG. 9C.
Figure 9F:
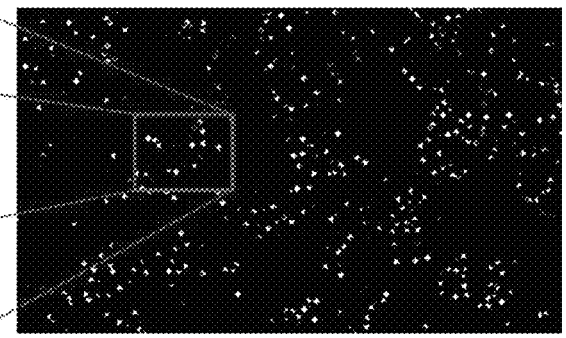
Figure 9G:
FIGS. 9G and 9H illustrate derived seed centers superimposed on each detected isolated spot in the spot channel image of FIG. 9C.
Figure 9H:
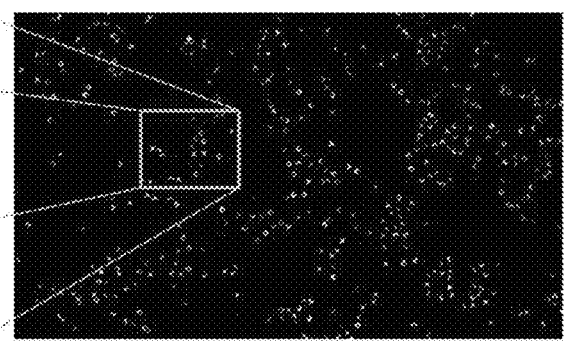
Figure 9I:
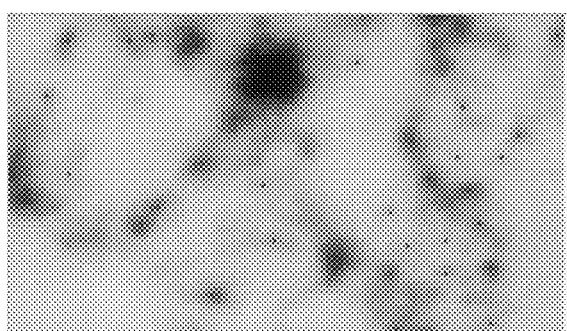
FIGS. 9I and 9J illustrate an overlay of the detected isolated spots superimposed on the portion of the whole slide image of FIG. 9A.
Figure 9J:
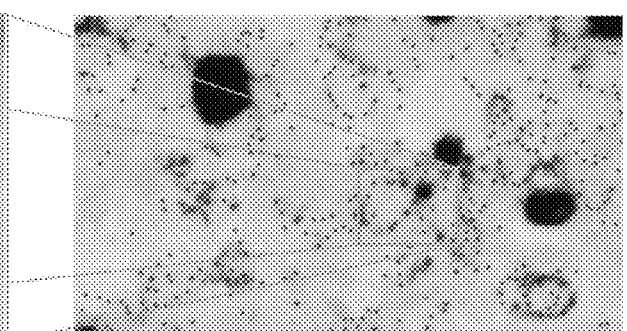

By way of example, and again in the context of KAPPA mRNA and LAMBDA mRNA detection, a black unmixed channel image (i.e. having signals corresponding to KAPPA mRNA gene copies) generated after unmixing may be used as an input image (see FIG. 9A corresponding to a portion of a whole slide image and FIG. 9B after unmixing the portion of the image) for detecting isolated KAPPA mRNA spots (i.e. single gene copies). In this particular, example, the isolated spot signals are extracted by detecting the disk-like shape of the spots using multiple pre-defined disk diameters. As illustrated in FIGS. 9C and 9D, blob and spot channel images are then separated after spot detection. Finally, the x,y coordinates of each detected isolated spot are calculated from the center seed of each spot signal, as illustrated in FIGS. 9E to 9 H. In some embodiments, an overlay may be generated, and the detected isolated spots are superimposed over the portion of the whole slide image used prior to unmixing (compared FIG. 9A with FIGS. 9I and 9J).

Figure 10A:
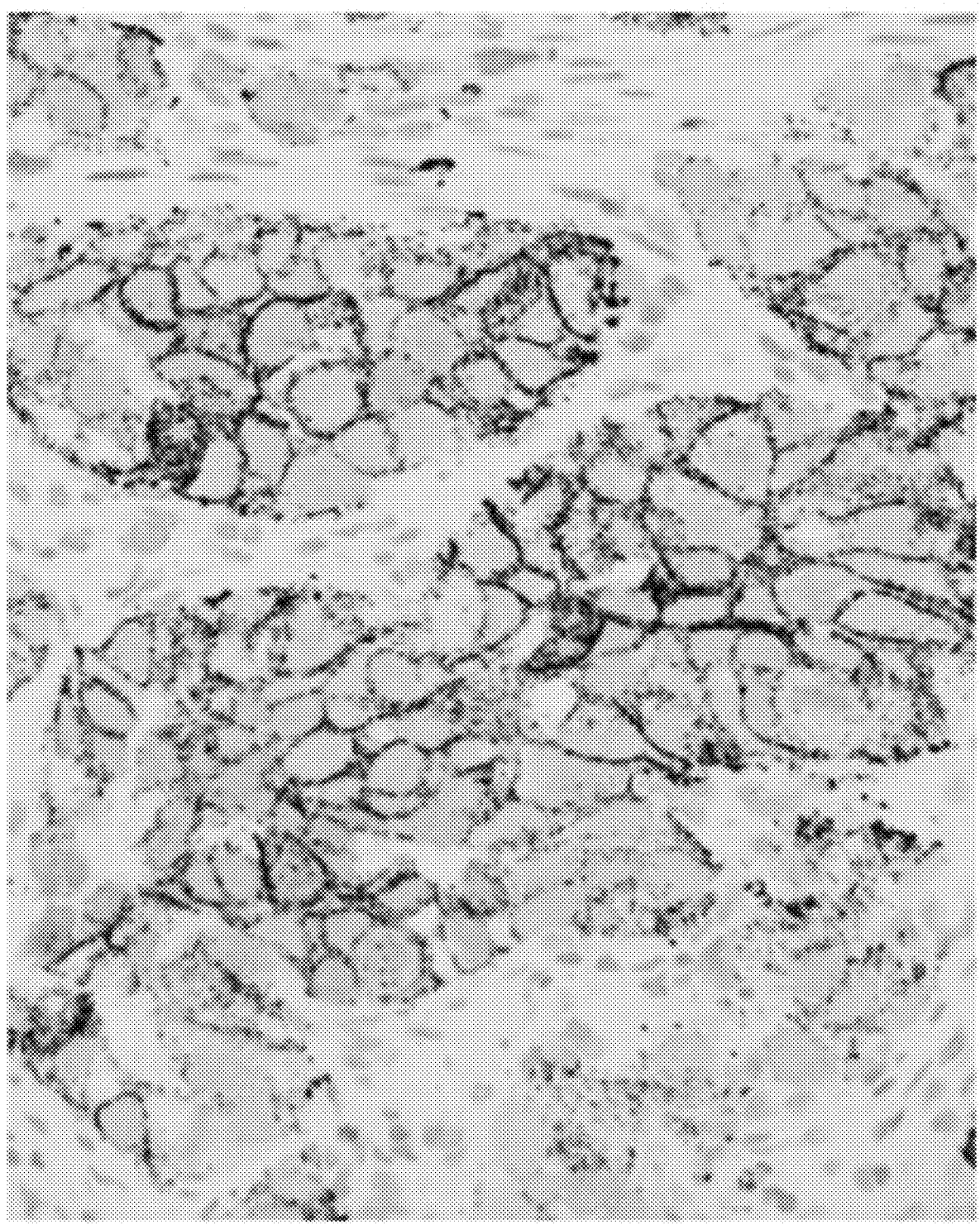
FIG. 10A illustrates a portion of whole slide image used as an input image in accordance with some embodiments of the present disclosure, wherein the biological sample in the whole slide image is stained for the presence of a protein biomarker (e.g. HER2).

By way of another example, and in the context of detecting the HER2 protein in images stained in an immunohistochemistry assay, FIG. 10A illustrates a portion of a whole slide image of a biological sample stained for the presence of the HER2 protein. FIGS. 10B and 10C illustrate the result of the detection of isolated spots in an unmixed image channel image derived from FIG. 10A, with the detected isolated spots superimposed over the portion of the whole slide image.

Optical Density Derivation Module

Following the detection of the isolated spots in an image (320), an optical density derivation module 205 is used to determinate an optical density of a representative isolated spot based on computed signal characteristics from each of the detected isolated spots (step 330), i.e. determining an optical density of a typical detected isolated spot considering certain characteristics of all detected isolated spots in the input image.

Figure 4:
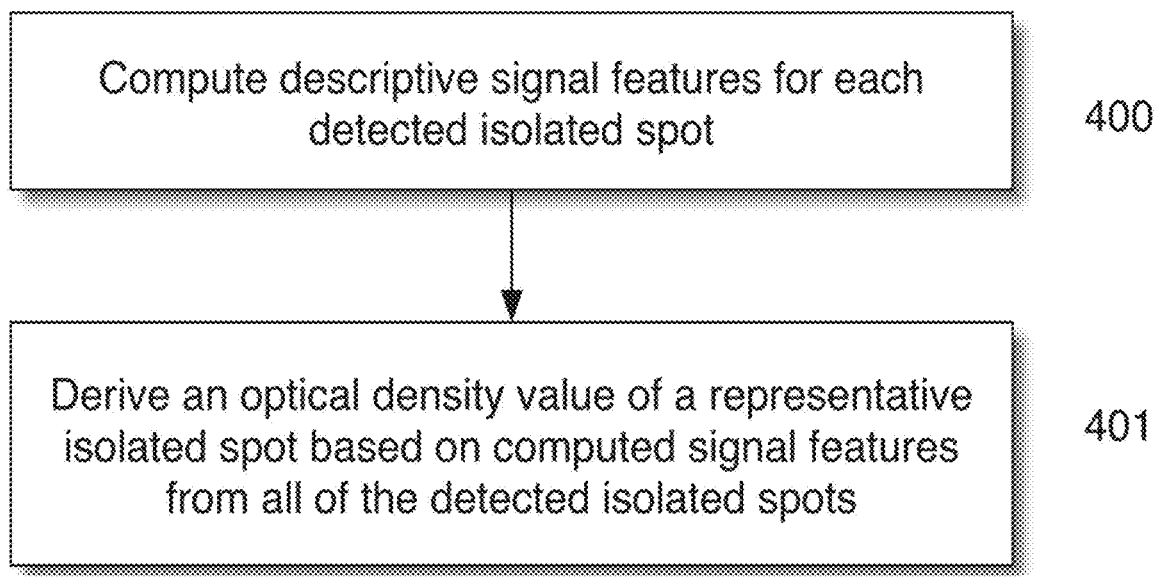
FIG. 4 sets forth a flowchart illustrating the generation of data from detected isolated spots, in accordance with some embodiments.

With reference to FIG. 4, in some embodiments, the optical density derivation module 205 first computes descriptive signal features for each of the detected isolated spots in the image (step 400). In some embodiments, the signal feature derivation module 205 implements a Gaussian fitting technique to analyze and parameterize certain characteristics of the detected isolated spots.

The phrase "Gaussian fitting" refers to fitting a curve of the data constituting a peak into a Gaussian distribution curve by determining constants of a Gaussian function. Here, data from each detected isolated spot from step 320 is used to generate a Gaussian function, whereby signal features, and hence characteristics from each detected isolated spot, may be derived. In some embodiments, the fitting method is performed based on the assumption that the distribution of the optical density and the radius is the normal distribution.

In some embodiments, a 1D-Gaussian-function fitting method is used to estimate the associated spot parameters within a pre-defined patch size surrounding a detected and isolated spot. In some embodiments, the patch size is 5×5 pixels. In other embodiments, the patch size is 7×7 pixels. In yet other embodiments, the patch size is 11×11 pixels. The skilled artisan will be able to determine the most appropriate patch size for any particular application that will facilitate the provisioning of optimal histogram results.

Figure 11:
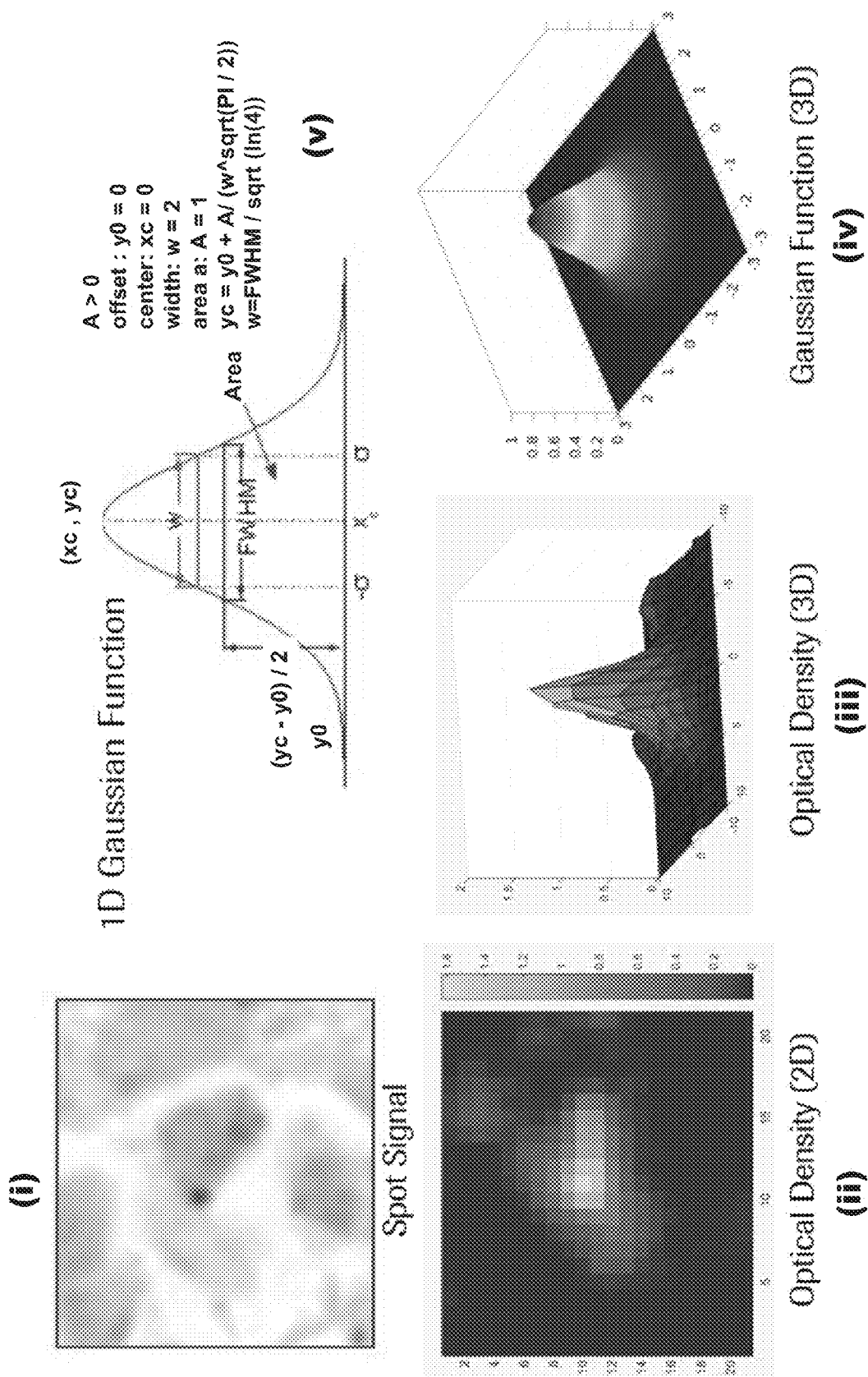
FIG. 11 illustrates the parameters which may be derived after a 1D-Gaussian fitting function to extract characteristics of detected isolated spots is employed on data derived from a patch surrounding a spot signal in accordance with some embodiments of the present disclosure. Panel (i) illustrates the window that crops the interested spot on the input image; panel (ii) illustrates the optical density of the cropped window from panel (i) displayed in 2D; panel (iii) illustrates the optical density of cropped window from panel (i) displayed in 3D; panel (iv) illustrates the 3D plot of the Gaussian function, where theoretically the Gaussian fitting method is used to determine the parameters of the input optical density to fit to a perfect Gaussian function; and panel (v) illustrates the 1D Gaussian function.

In some embodiments, the characteristics derived from the Gaussian fitting technique include the size, intensity, blurriness, and roundness of the detected isolated dots, and each of these characteristics are computed using parameters of the Gaussian function. In some embodiments, by solving the linear system Ax=b, the estimated parameters from the fitting method consist of mean, standard deviation (SD), and full-width-at-half maximum, such as illustrated in FIG. 11.

In some embodiments, an intensity characteristic of a detected isolated spot is computed using the 98th percentile within a radius of 5 pixels surrounded the center of the detected spots. In other embodiments, the whole range of intensity in the intensity histogram may be used to compute the intensity of the representative isolated spot by weighting the intensity with its histogram bin number and dividing by the summation of the intensity value (e.g. intensityRef= sum(hIntensity.Values.*(hIntensity.BinEdges))/ sum(hIntensity.Values))

In some embodiments, the radius for the representative isolated spot is computed by solving: (sizeRef=sum (hSize.Values.*(hSize.BinEdges))/sum(hSize.Values).

In other embodiments, a blurriness characteristic is derived by finding the standard deviation (σ) of the Gaussian-function fitting method.

In yet other embodiments, a size characteristic is derived from the width at half maximum (FWHM). FWHM is an expression of the extent of a function given by the difference between the two extreme values of the independent variable at which the dependent variable is equal to half of its maximum value. In other words, it is the width of a spectrum curve measured between those points on the y-axis which are half the maximum amplitude (see, e.g. FIG. 11). FWHM is computed using the following equation:

$$FWHM = 2\sqrt{2\ln 2}\ \sigma \approx 2.355\sigma$$

In further embodiments, a roundness characteristic is computed based on the comparison between the actual optical density distribution within a patch and a perfect Gaussian model computed from the estimated parameters. The concordance correlation coefficient (CCC) (which measures the agreement between two variables, e.g., to evaluate reproducibility or for inter-rater reliability) may be to compare the relationship (or the agreement), where CCC=1 shows that the estimated parameters are perfectly agreement to the ideal Gaussian model; and where CCC=0 shows that there is no agreement between the estimated parameters and the ideal Gaussian model.

Referring again to FIG. 4, once signal feature characteristics of each detected isolated spot are determined, an optical density of a representative isolated spot may be derived (step 401).

Figure 5:
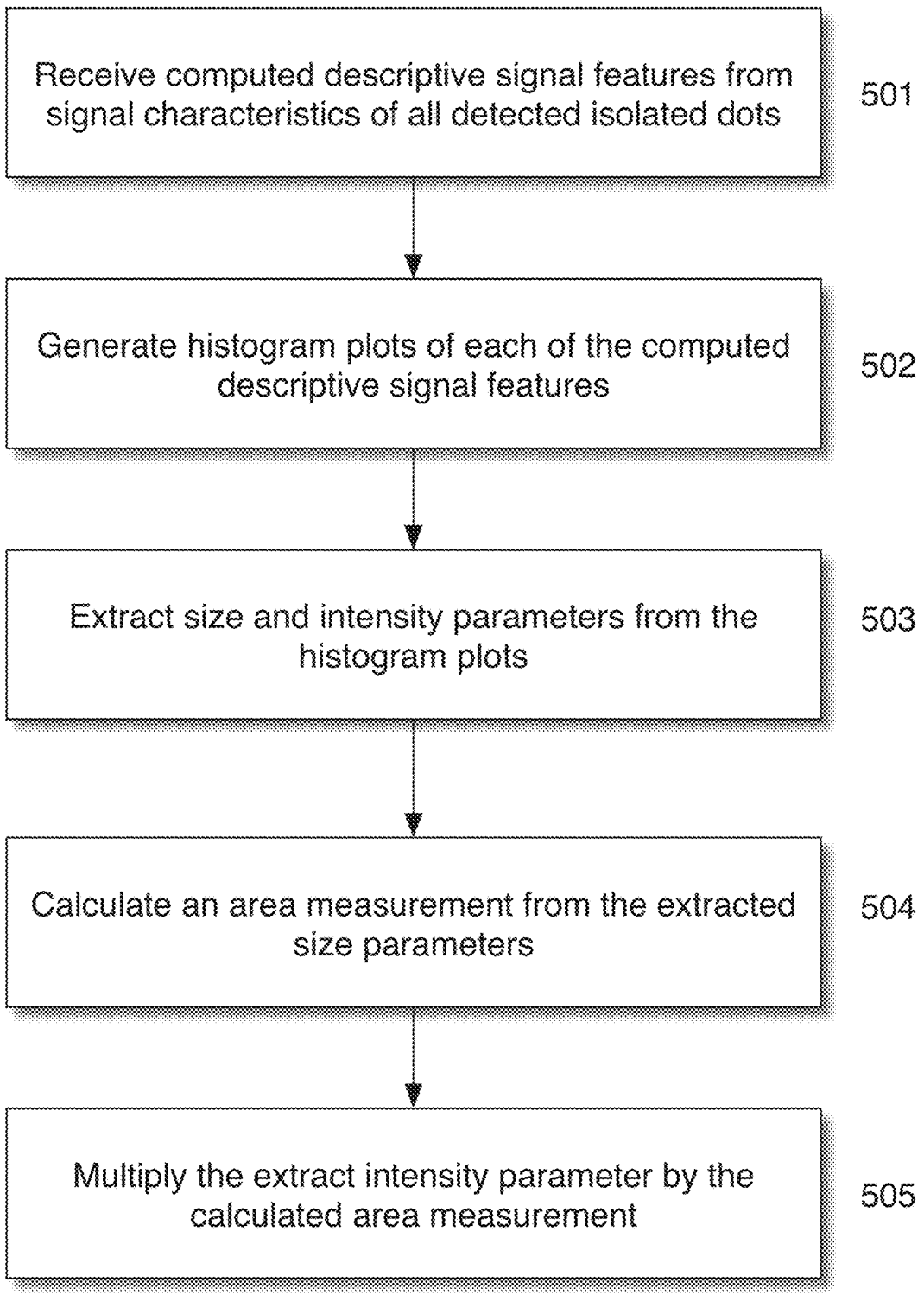
FIG. 5 sets forth a flowchart illustrating the steps of computing an optical density value of a representative isolated spot, in accordance with some embodiments.
Figure 6A:
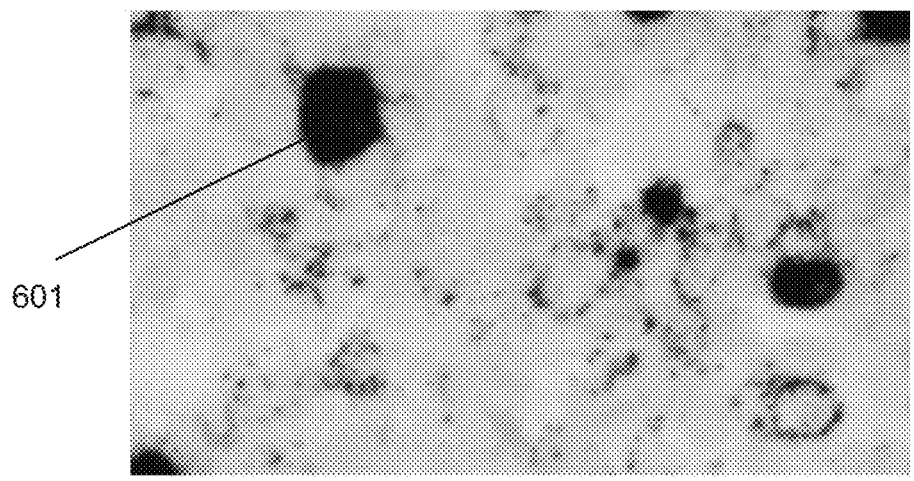
FIG. 6A provides a portion of a whole slide image stained in an in situ hybridization assay with KAPPA mRNA (silver or black color/reporter, 601) with counterstain hematoxylin.
Figure 6B:
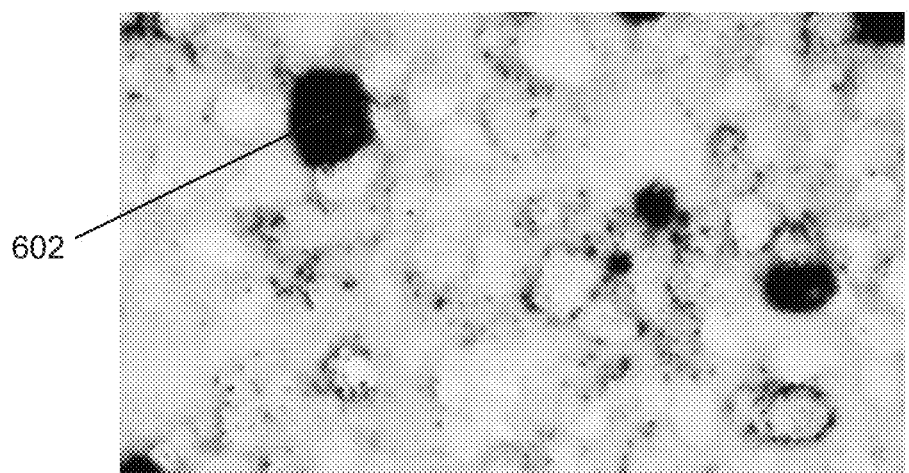
FIG. 6B provides an example of an image channel image after unmixing, showing only signal corresponding to KAPPA mRNA (silver/black color/reporter, 602).
Figure 6C:
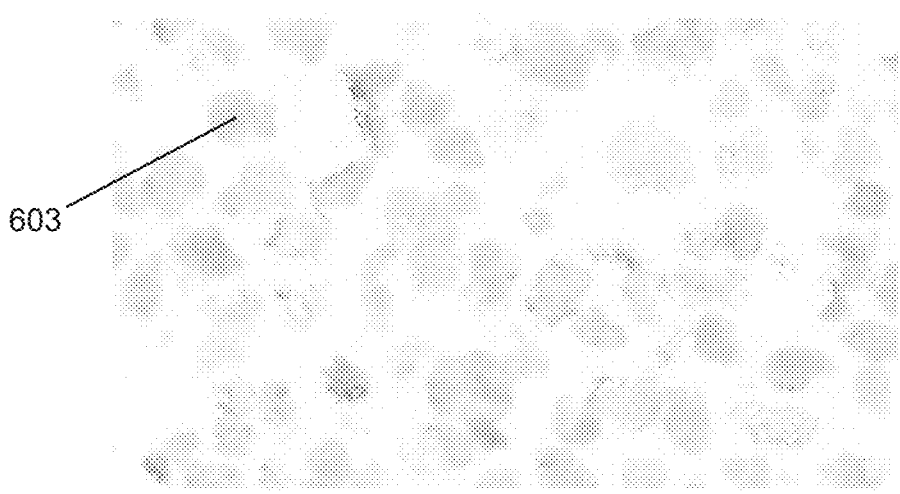
FIG. 6C provides an example of an image channel after unmixing, showing a hematoxylin channel (e.g. blue, 603).
Figure 7A:
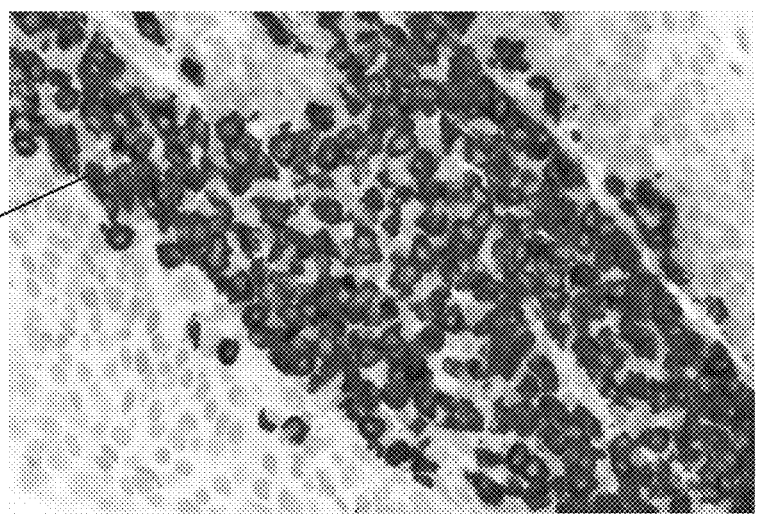
FIG. 7A provides a portion of a whole slide image stained in an in situ hybridization assay with LAMBDA mRNA probes (purple color/reporter, 701) with counterstain hematoxylin.
Figure 7B:
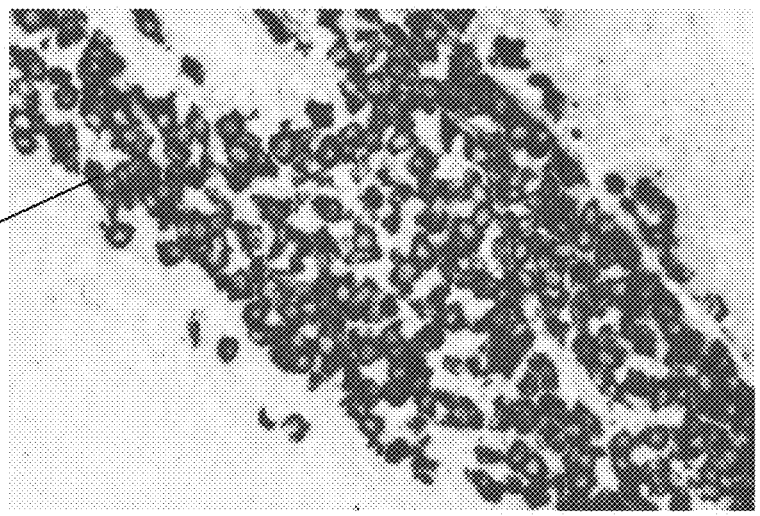
FIG. 7B provides an example of an image channel image after unmixing, showing only signal corresponding to LAMBDA mRNA (purple color/reporter, 702).
Figure 7C:
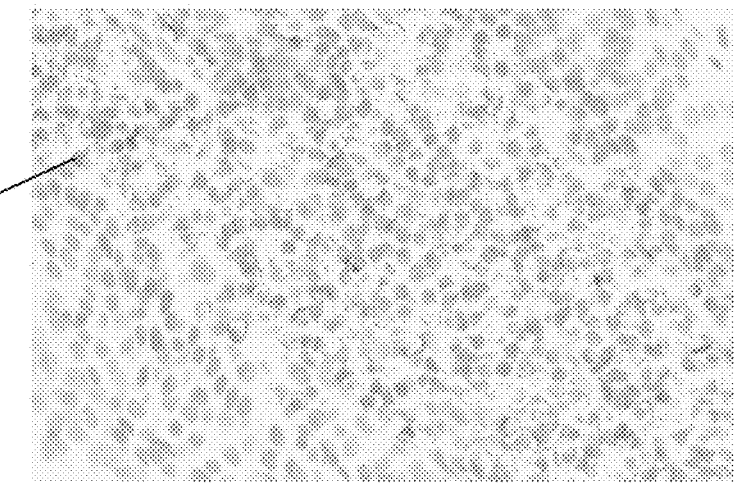
FIG. 7C provides an example of an image channel after unmixing, showing a hematoxylin channel (e.g. blue, 703).
Figure 8A:
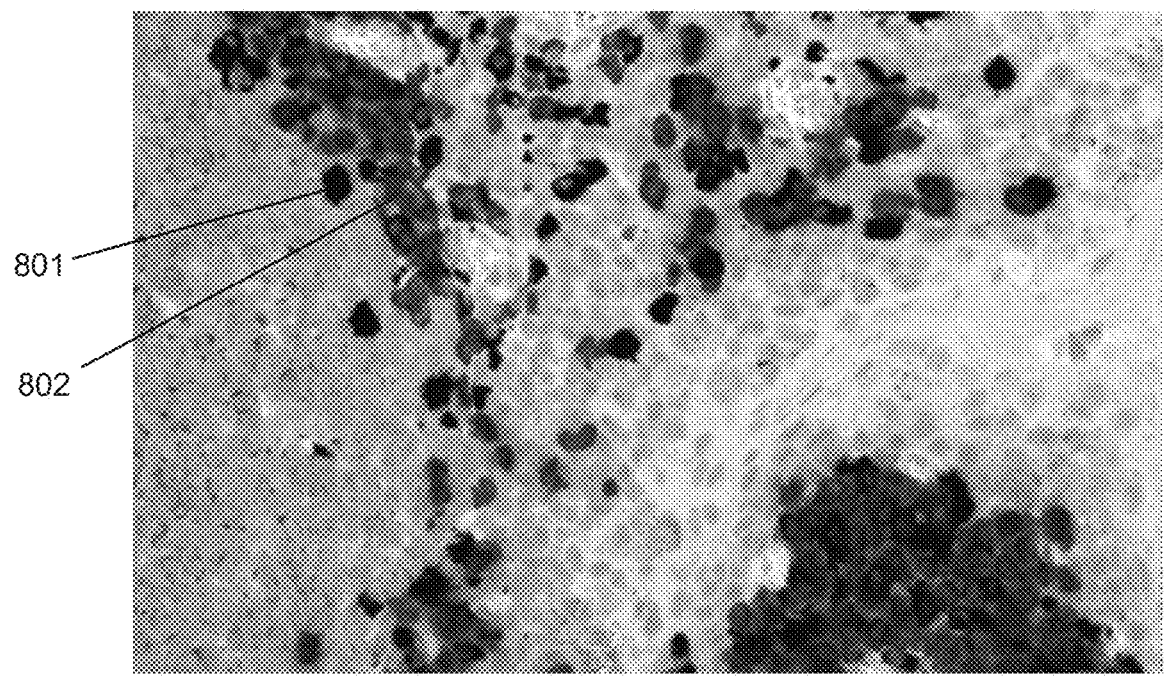
FIG. 8A provides a portion of a whole slide image stained in an in situ hybridization assay with KAPPA mRNA (silver or black color/reporter, 801) and LAMBDA mRNA probes (purple color/reporter, 802).
Figure 8B:
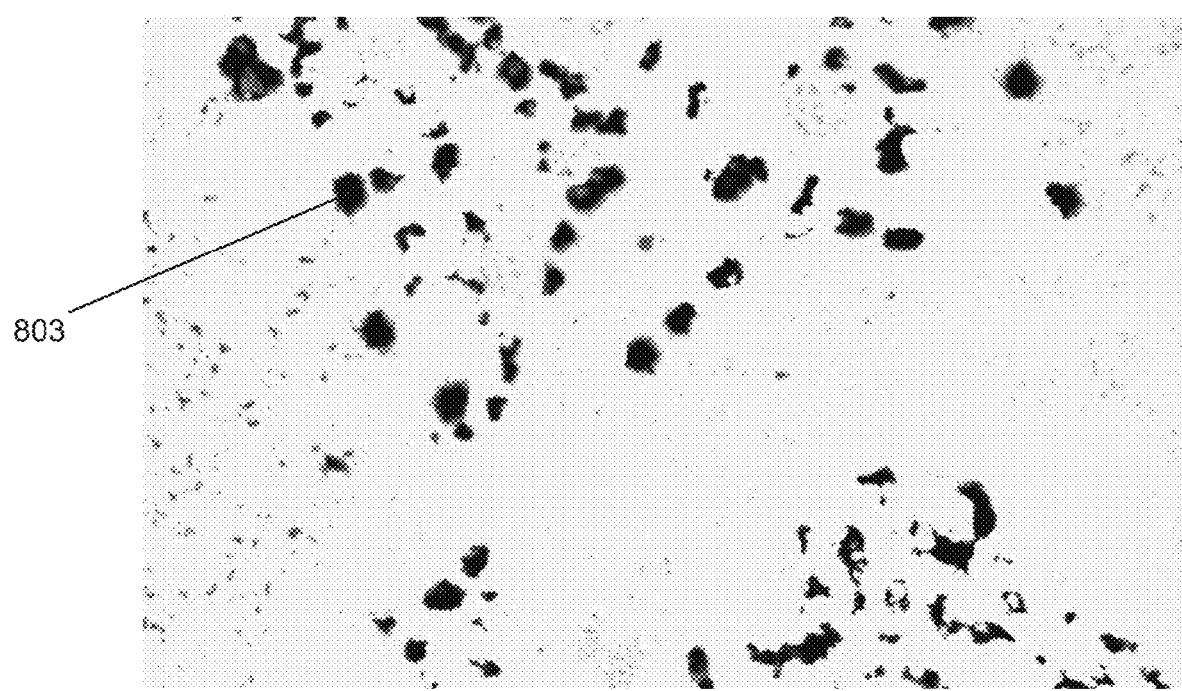
FIG. 8B provides an example of an image channel image after unmixing, showing only signal corresponding to KAPPA mRNA (black color/reporter, 803).
Figure 8C:
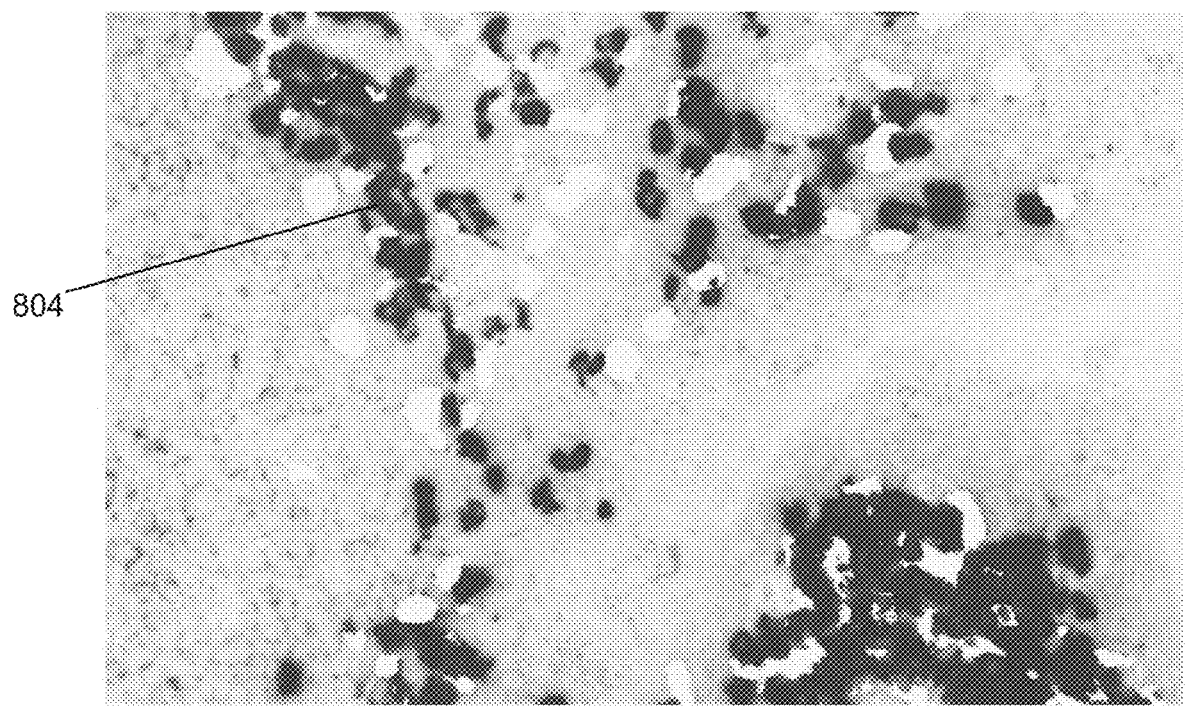
FIG. 8C provides an example of an image channel image after unmixing, showing only signal corresponding to LAMBDA mRNA (purple color/reporter, 804).
Figure 8D:
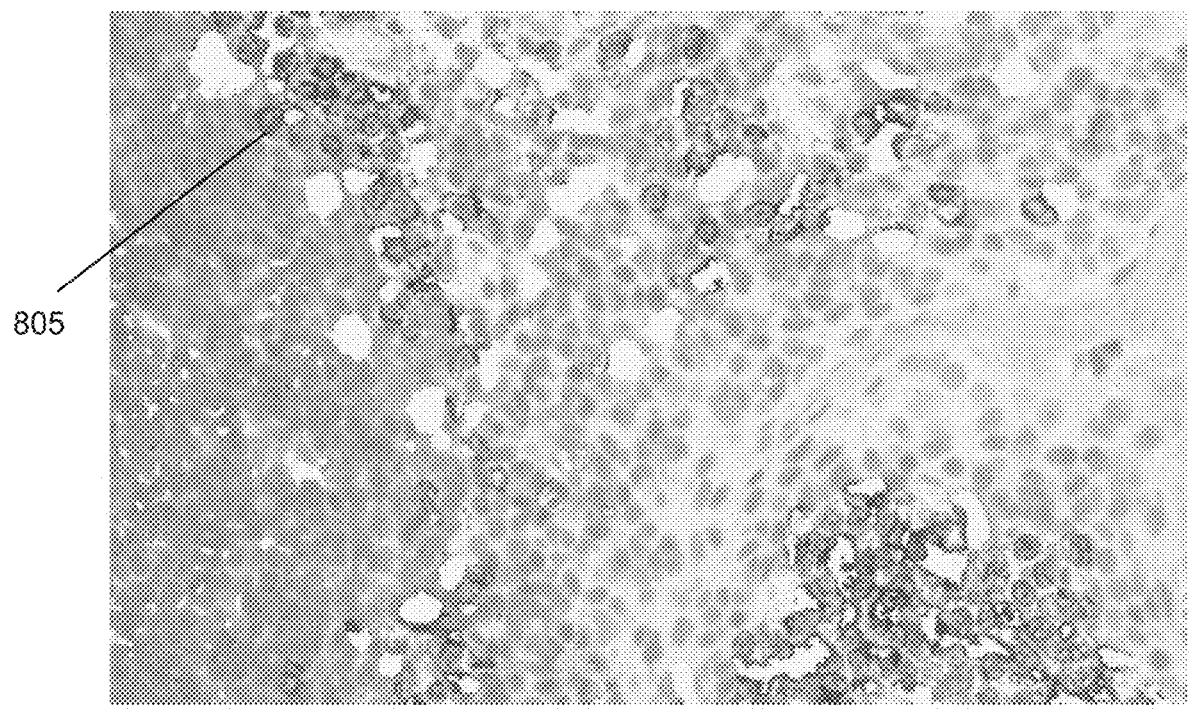
FIG. 8D provides an example of an image channel after unmixing, showing a hematoxylin channel (e.g. blue, 805).
Figure 12:
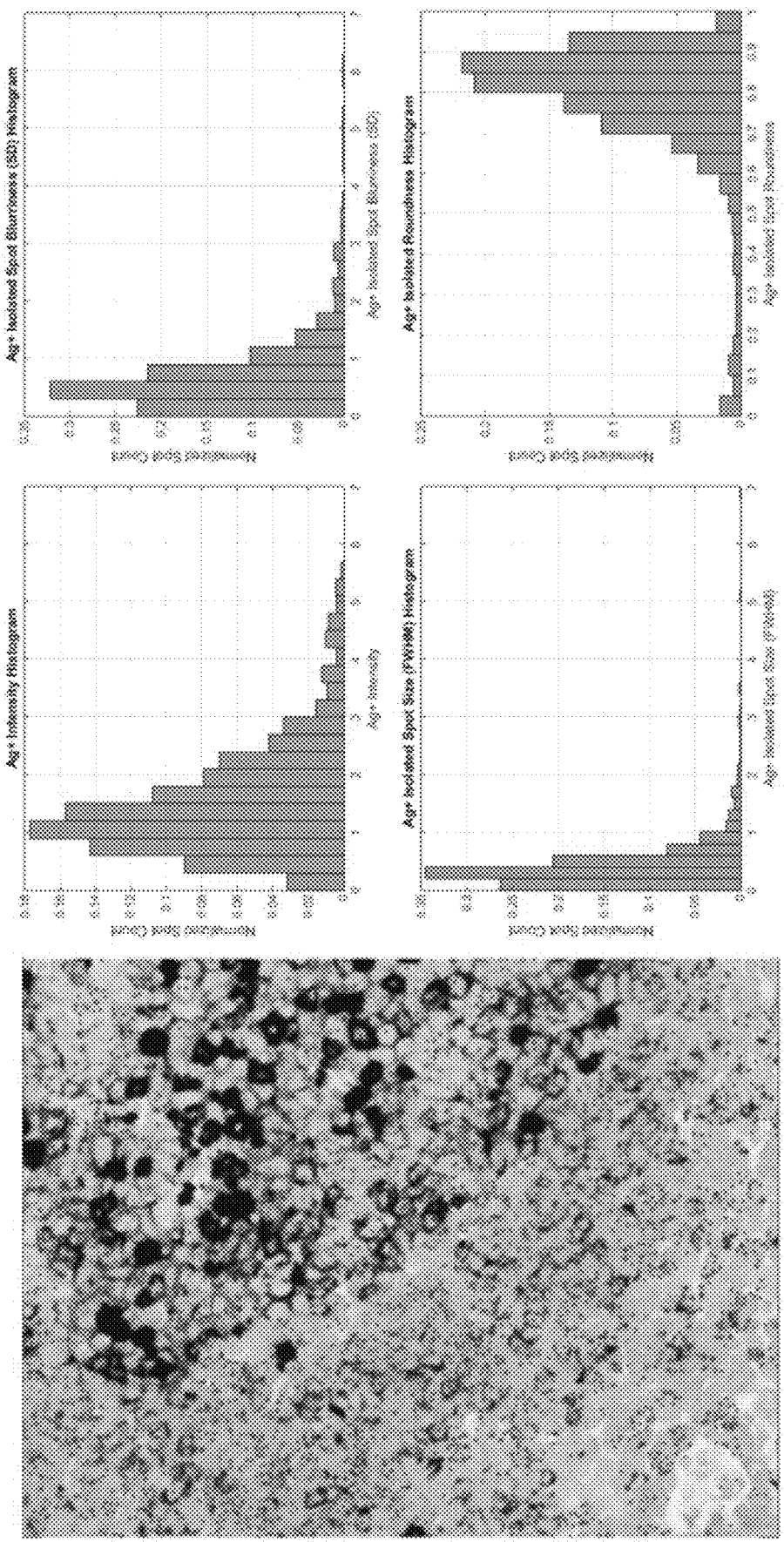
FIG. 12 illustrates a result of spot detection and the generation of computed parameters from the each of the detected isolated spots, where the computed parameters are binned into several different histograms, in accordance with some embodiments of the present disclosure.

FIG. 5 provides a flowchart illustrating the steps of calculating the optical density of a representative isolated spot. As a first step of the process, the computed descriptive signal features (from step 400) are received as input (501). Next, histograms may be generated for each computed signal feature characteristic (step 502). For example, if FWHM parameters representing the size of isolated spots are determined, a histogram of the FMHM parameters may be generated. In some embodiments, the generated histograms illustrate the distribution of isolated spots in the input image having certain values for each of the signal feature characteristics, such as illustrated in FIG. 12. In some embodiments, the y-axis of each histogram provides the normalized spot count while the x-axis sets forth the feature quantity. For example, in FIG. 12, a histogram is presented which shows the intensity of black dot signals and the number of detected isolated spots having each of a series of binned intensity values. Likewise, FIG. 12 illustrates a histogram which shows the distribution of detected isolated spots having a particular binned size.

As such, the generated histograms provide for an understanding of the density of detected isolated cells that have particular values or representative characteristics. The skilled artisan will appreciate that the generated histograms therefore provide insight into the characteristics of a representative or typical detected isolated spot. For example, by looking at an intensity histogram (e.g. FIG. 12), the skilled artisan would be able to determine that the intensity value of the detected isolated spots that is repeated most often (i.e. the mode of the intensity values) has a certain value (e.g. a value of 0.9). The assumption could then be made that a representative or typical detected isolated spot would have that particular determined intensity value (e.g. 0.9). In other embodiments, a weight average value, for example, may be utilized.

Given the foregoing, the next step is to extract size and intensity parameters from the generated histogram plots (step 502) such that the following equation may be solved:

$$\sum OD_s = \text{Area} \times \overline{OD_S}$$

where Area can refer to a circle ($\pi r^2$) or a rectangle (w×h) area assumed to be a shape of a spot, and $\overline{OD}_s$ refers to a prospective optical density of a single dot.

In some embodiments, the prospective optical density of a single dot is an intensity value, which may be a uniform or non-uniform intensity value. In some embodiments, the prospective optical density of a single dot may be a mode of the intensity histogram, an average of the total intensity of the total detected isolated spots, or a weighted intensity, or a weighted average intensity of histogram. etc. In some embodiments, the isolated signal characteristics derived and then the parameters, e.g. size, intensity, etc., are used as a descriptive statistic to model an individual spot in that current data (image) to compute the estimated count of the aggregated signal. The model of an individual spot could be a simple or a more complex model such as a circle, a rectangular, a sphere, or a 3D sphere that have signal density varies (with blurriness) from the center to the boundary.

Next, an area measurement is calculated (step 504) from the extracted size parameters (from step 503). For example, a radius may be derived from a mode of the FWHM values in the respective histogram plot. This radius may then be multiplied by Pi to arrive at the area.

By way of a further example, the following data may be calculated such that the optical density of a representative isolated spot may be derived:

(i) Select threshold (e.g., TH=0.45) of the background intensity using the percentile 10 of a silver spot intensity histogram plot.

(ii) Use a mode of silver intensity histogram (intensity=0.9) as a prospective intensity of isolated dots.

(iii) Use the size of FWHM=1.06 using a percentile 10 of a silver spot size histogram plot to be a prospective size of a representative isolated dots.

Finally, the derived intensity parameter is multiplied by the area to give the optical density of a representative isolated spot (step 505). The computed optical density of a representative spot is then supplied to the spot estimation module 208.

Segmentation Module and Residual Image Generation Module

In some embodiments, prior to estimating a number of predictive spots in signal aggregates, the input image is segmented into a plurality of sub-regions using segmentation module 207. In some embodiments, the generation of sub-regions is believed to minimize computation error due to the fact that the computations are based on a smaller local regions rather an entire image. In some embodiments, segmentation of the input image into a plurality of sub-regions is useful to reduce the complexity in estimating signal in the aggregate signal blobs. In some embodiments, segmentation provides a plurality of sub-regions where staining presence (e.g. pixels present in the superpixel are of a particular type of stain), staining intensity (e.g. pixels have a certain relative intensity value or range of values), and/or texture (e.g. pixels have a particular spatial arrangement of color or intensities) are similar or uniform. Having a sub-region that is substantially uniform is especially important for segments that consist nearly entirely of aggregate signal, the uniformity across the sub-region creating a consistent approximation of the spot count within that segment during signal estimation (described herein). Segmentation is performed on a single channel image, e.g. a "purple" channel in an unmixed image showing single for LAMBDA mRNA or a "black" channel in an unmixed image showing signal for KAPPA mRNA.

Figure 13:
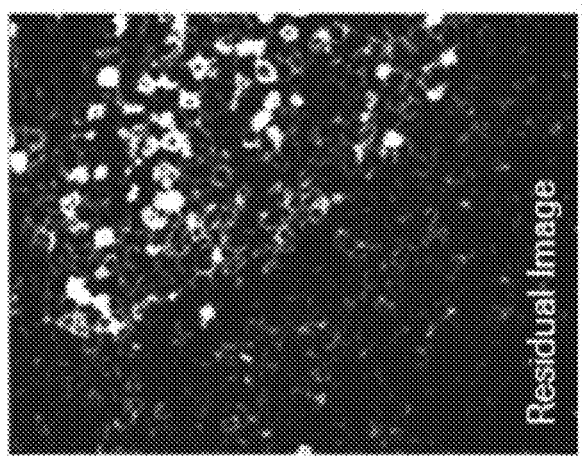
FIG. 13 illustrates the generation of a residual image, in accordance with some embodiments of the present disclosure, from an unmixed image channel image and a spot channel image, where the residual image is substantially free of signals from the detected isolated spots shown in the spot channel image, in accordance with some embodiments of the present disclosure.
Figure 13:
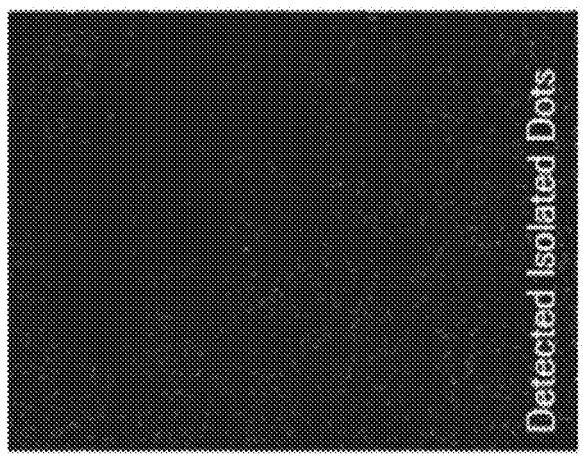
Figure 13:
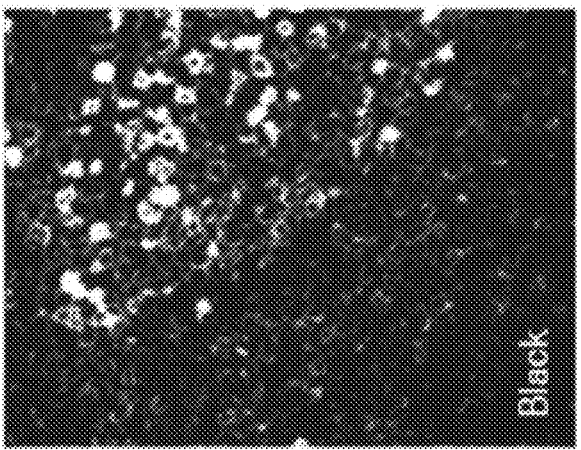

In some embodiments, segmentation is performed on an image which is different than the image used to detect the isolated spots, or which was used to compute the optical density of a representative or typical isolated spot. In some embodiments, segmentation is performed on a residual image generated by a residual image generation module 206. In some embodiments, the residual image is generated by subtracting one image from another image. For example, an isolated spots image (as described herein) may be subtracted from an unmixed image channel image to provide a residual image having only signal aggregate blobs. In other embodiments, a foreground segmentation mask may be generated based on the location of the detected isolated spots, and the foreground segmentation mask may be used to filter an unmixed image channel image to provide a residual image having only signal aggregate blobs. An example of a residual image is provided in FIG. 13.

In some embodiments, the sub-regions generated capture information in an area of the input image having either a pre-determined size or a size within a range as set forth within an image processing algorithm (e.g. a parameter of a SLIC superpixel generation algorithm as described herein).

In some embodiments, the input image is segmented into sub-regions having a predefined shape, size, area, and/or spacing. For example, the sub-regions may be ovals, circles, squares, rectangles, etc. In some embodiments, the oval, circular, square, or rectangular sub-regions may have a size ranging from between 50 pixels to about 100 pixels, or some other size such that groups of pixels are selected having similar properties. In some embodiments, the sub-regions are non-overlapping, and may be generated via a sampling grid. In some embodiments, the sub-regions are distributed across the image in a manner that captures a representative sample of relevant regions for analysis, e.g. areas where irregularly shaped cells are a predominant feature.

In other embodiments, the input image is segmented by applying a series of algorithms to the image, including global thresholding filters, local adaptive thresholding filters, morphological operations, and watershed transformations. The filters may be run sequentially or in any order deemed necessary by those of ordinary skill in the art. Of course, any filter may be applied iteratively until the desired outcome is achieved. In some embodiments, a first filter is applied to the input image to remove regions that are unlikely to have stain, such as removing those image regions that are white. In some embodiments, this is achieved by applying a global thresholding filter. In some embodiments, the global thresholding is based on a median and/or standard deviation computed on a first principal component channel, e.g. similar to a gray scale channel. Filters are then applied to the image to selectively remove artifacts, e.g. small blobs, small discontinuities, other small objects, and/or to fill holes. In some embodiments, morphological operators are applied to remove artifacts and/or fill holes. In some embodiments, a distance-based watershed is applied, based on a binary image introduced as input (e.g. a binary image resulting from prior filtering steps).

Figure 14A:
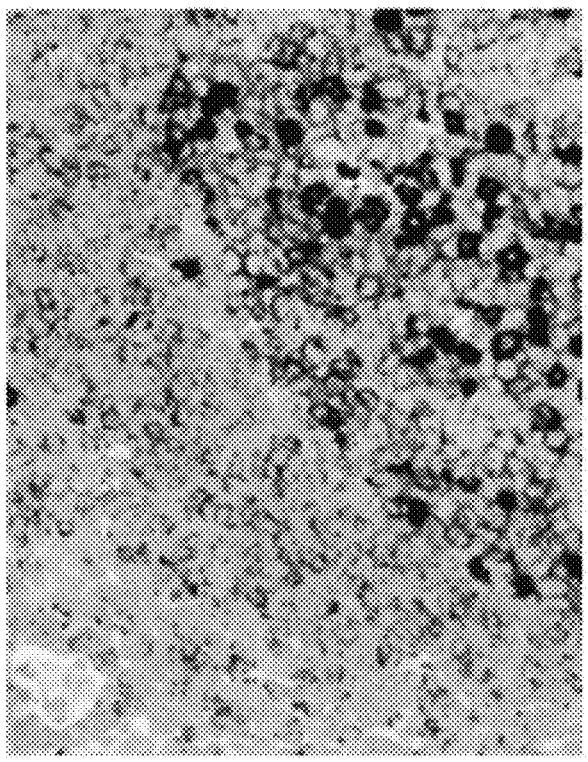
FIG. 14A illustrates a portion of a whole slide image stained with at least one biomarker in accordance with some embodiments of the present disclosure.
Figure 14B:
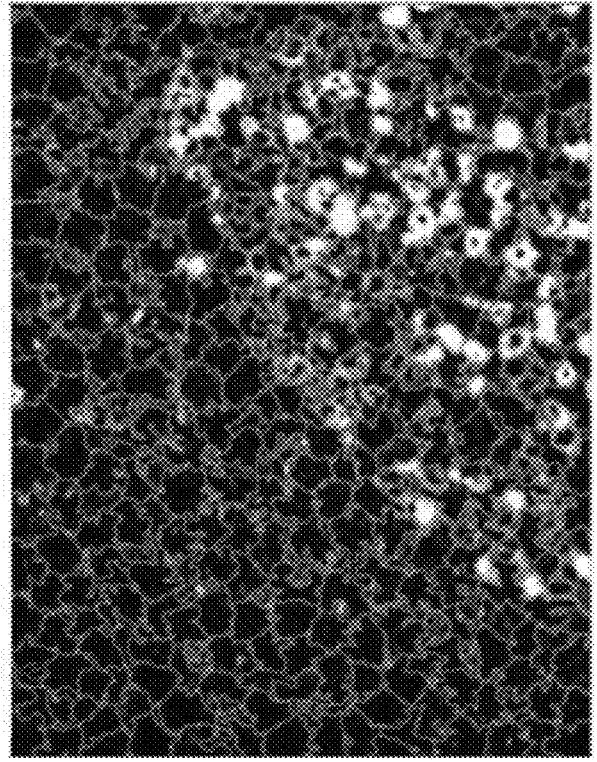
FIG. 14B illustrates the result of segmentation of the portion of the whole slide image of FIG. 14A in accordance with some embodiments of the present disclosure.
Figure 14C:
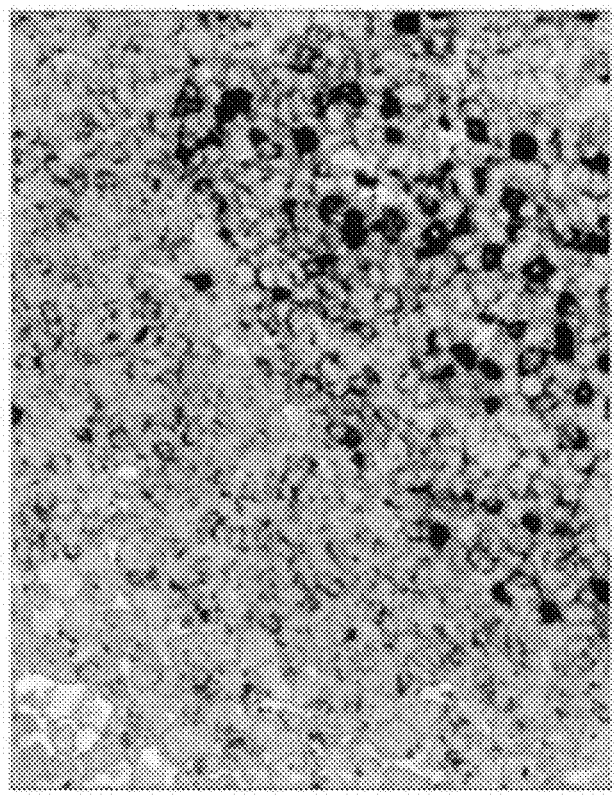
FIG. 14C illustrates the result of superimposing the generated segments onto the portion of the whole slide image in accordance with some embodiments of the present disclosure.

In some embodiments, the input image is segmented into superpixels. It is believed that a superpixels algorithm partitions an image into a number of segments (group of pixels) that represent perceptually meaningful entities. Each superpixel is obtained by a low-level grouping process and has a perceptually consistent unit, i.e., all pixels in a biological object contained in a superpixel are as uniform as possible in staining presence, staining intensity, and texture. An example of superpixel segmentation is illustrated in FIGS. 14A to 14C (where FIG. 14A illustrates a portion of a whole slide image; FIG. 14B illustrates superpixel generation on an unmixed image channel image free of the detected isolated spots, i.e. a residual image; and 14C illustrates the generated superpixels superimposed over the portion of the whole slide image from FIG. 14A). As will be described further herein, the superpixel segmented image (e.g. FIG. 14B) may be used as input for estimating an amount of signal corresponding to a biomarker in each signal aggregate blob.

A superpixel is a collection of pixels with similar characteristics, such as color, brightness, and texture. An image can be composed of a certain number of superpixels that contain multiple combination characteristics of the pixels and can preserve the edge information of the original image. Compared with a single pixel, a superpixel contains rich characteristic information and can greatly reduce image post-processing complexity and significantly increase the speed of image segmentation. Superpixels are also useful for estimating probabilities and making decisions with small neighborhood models.

Superpixel algorithms are methods that group pixels into meaningful atomic regions of similar size. Without wishing to be bound by any particular theory, it is believed that superpixels are powerful because they often fall on important boundaries within the image and tend to take on abnormal or unique shapes when they contain salient object features. Consistent with the desire to obtain and store information at a medium resolution analysis, superpixels are located between pixel- and object-level: they carry more information than pixels by representing perceptually meaningful pixel groups, while not comprehensively representing image objects. Superpixels can be understood as a form of image segmentation, that over-segment the image in a short computing time. The outlines of superpixels have shown to adhere well to natural image boundaries, as most structures in the image are conserved. With image features being computed for each superpixel rather than each pixel, subsequent processing tasks are reduced in complexity and computing time. Thus, superpixels are considered useful as a preprocessing step for analyses at object level such as image segmentation.

Without wishing to be bound by any particular theory, it is believed that superpixels over-segment an image by forming compact and uniform groups of pixels that have similar characteristics in e.g., color or geometry. In the past, multiple superpixel approaches have been developed. They can be classified into (i) graph-based and (ii) gradient-ascent-based approaches. In a graph-based approach, each pixel is considered a node in a graph. An edge weight is defined between all pairs of nodes that is proportional to their similarity. Then, a cost function defined on the graph is formulated and minimized, in order to extract superpixel segments. In a gradient-ascent-based approach, pixels are iteratively mapped to a feature space to delineate denser regions that represent clusters. Each iteration refines each cluster to obtain a better segmentation until convergence.

Many superpixel algorithms have been developed, including normalized cuts, agglomerative clustering, quick shift and Turbopixel algorithms. The Normalized cuts algorithm recursively partitions a graph of all pixels in the image using contour and texture cues, globally minimizing a cost function defined on the edges at the partition boundaries. It produces very regular, visually pleasing superpixels (see Jianbo Shi and Jitendra Malik. Normalized cuts and image segmentation, IEEE Transactions on Pattern Analysis and Machine Intelligence, (PAMI), 22(8):888-905, August 2000, the disclosure of which is incorporated by reference herein in its entirety). Alastair Moore, Simon Prince, Jonathan Warrell, Umar Mohammed, and Graham Jones. Superpixel Lattices. IEEE Computer Vision and Pattern Recognition (CVPR), 2008, describe a method to generate superpixels that conform to a grid by finding optimal paths, or seams, that split the image into smaller vertical or horizontal regions. Optimal paths are found using a graph cuts method (see, Shai Avidan and Ariel Shamir. Seam carving for content-aware image resizing. ACM Transactions on Graphics (SIGGRAPH), 26(3), 2007, the disclosure of which are hereby incorporated by reference herein). Quick shift (see A. Vedaldi and S. Soatto). Quick shift and kernel methods for mode seeking. In European Conference on Computer Vision (ECCV), 2008, the disclosure of which is hereby incorporated by reference herein) uses a mode-seeking segmentation scheme. It initializes the segmentation using a medoid shift procedure. It then moves each point in the feature space to the nearest neighbor that increases the Parzen density estimate. The Turbopixel method progressively dilates a set of seed locations using level-set based geometric flow (see A. Levinshtein, A. Stere, K. Kutulakos, D. Fleet, S. Dickinson, and K. Siddiqi). Turbopixels: Fast superpixels using geometric flows. IEEE Transactions on Pattern Analysis and Machine Intelligence (PAMI), 2009, the disclosure of which is incorporated by reference herein). The geometric flow relies on local image gradients, aiming to regularly distribute superpixels on the image plane. Unlike other methods, the Turbopixel superpixels are constrained to have uniform size, compactness, and boundary adherence. Yet other methods of generating superpixels are described by Radhakrishna Achanta, "SLIC Superpixels Compared to State-of-the-art," Journal of Latex Class Files, Vol. 6, No. 1, December 2011, the disclosure of which is incorporated by herein in its entirety).

A superpixel algorithm called simple linear iterative clustering (SLIC) has been introduced, which, compared to the state-of-the-art superpixel methods, is superior for both boundary adherence and efficiency. The SLIC has two steps. Firstly, it generates superpixels by grouping pixels with a local k-means clustering (KMC) method, where the distance is measured as the Euclidean distance integrated with the data and spatial distances. Secondly, a connected components algorithm (CCA) is used to remove the generated small isolated regions by merging them into the nearest large superpixels.

k-means clustering aims to partition n observations into k clusters in which each observation belongs to the cluster with the nearest mean, serving as a prototype of the cluster. Connected component labeling works by scanning an image, pixel-by-pixel (from top to bottom and left to right) in order to identify connected pixel regions, i.e. regions of adjacent pixels which share the same set of intensity values V. (For a binary image V={1}; however, in a graylevel image V will take on a range of values, for example: V={51, 52, 53, . . . , 77, 78, 79, 80}.) Connected component labeling works on binary or graylevel images and different measures of connectivity are possible. However, for the following we assume binary input images and 8-connectivity. The connected components labeling operator scans the image by moving along a row until it comes to a point p (where p denotes the pixel to be labeled at any stage in the scanning process) for which V={1}. When this is true, it examines the four neighbors of p which have already been encountered in the scan (i.e. the neighbors (i) to the left of p, (ii) above it, and (iii and iv) the two upper diagonal terms). Based on this information, the labeling of p occurs as follows: If all four neighbors are 0, assign a new label to p, else if only one neighbor has V={1}, assign its label to p, else if more than one of the neighbors have V={1}, assign one of the labels to p and make a note of the equivalences.

After completing the scan, the equivalent label pairs are sorted into equivalence classes and a unique label is assigned to each class. As a final step, a second scan is made through the image, during which each label is replaced by the label assigned to its equivalence classes. For display, the labels might be different graylevels or colors.

SLIC is an adaptation of k-means for superpixel generation, with two important distinctions: (i) the number of distance calculations in the optimization is dramatically reduced by limiting the search space to a region proportional to the superpixel size (this is believed to reduce the complexity to be linear in the number of pixels—and independent of the number of superpixels k); and (ii) a weighted distance measure combines color and spatial proximity while simultaneously providing control over the size and compactness of the superpixels. (See Achanta, et al., "SLIC Superpixels Compared to State-of-the-Art Superpixel Methods," IEEE Transactions on Pattern Analysis and Machine Intelligence, Vol. 34, No. 11, November 2012, the disclosure of which is hereby incorporated by reference in its entirety herein).

SLIC considers image pixels in a 5D space, defined by the L*a*b values of the CIELAB color space as well as their x and y coordinates. Pixels in the 5D space are clustered based on an adapted k-means clustering integrating color similarity and proximity in the image plane. The clustering is based on a distance measure D that measures color similarity in L*a*b space (dc) and pixel proximity in x, y space (ds). The latter is normalized by a grid interval (S) that defines the square root of the total number of image pixels divided by the number of superpixels (k). The compactness and regularity of the superpixels is controlled with the constant m. This parameter functions as a weighting criteria between the spatial distance (dc) and the spectral distance (ds). A larger m, increases the weight of spatial proximity, which leads to more compact superpixels with boundaries adhering less to spectral outlines in the image.

$$D = \sqrt{\left(\frac{d_c}{m}\right)^2 + \left(\frac{d_s}{S}\right)^2} \qquad \text{(Eq. 1)}$$

The SLIC algorithm may be applied as follows. Let $N_p$ be the number of pixels in a given image (or portion or region of interest thereof) and k the number of superpixels to generate. Next, the main steps of the SLIC algorithm are as follows:

(1) Initialize cluster centers. Set k initial cluster centers on a regular grid spaced $S=\sqrt{N_p/k}$ pixels apart, and then move these cluster centers to the positions with the lowest gradients in a 3×3 neighborhood. Without wishing to be bound by any particular theory, it is believed that is done to avoid centering a superpixel on an edge, and to reduce the chance of seeding a superpixel with a noisy pixel.

(2) Assign pixels. Designate each pixel to a closest cluster center in a local search space by local KMC.

(3) Update cluster centers. Set each cluster center as the mean of all pixels in the corresponding cluster.

(4) Repeat steps (2)-(3) until the clusters do not change or another given criterion is met.

(5) Post-processing. The CCA is used to reassign isolated regions to nearby superpixels if the size of the isolated regions is smaller than a minimum size $S_{min}$.

A local KMC is applied in step (2) of the SLIC method, where each pixel is associated with the closest cluster center whose search area covers its location. In conventional KMC, the search area of each cluster center is the whole image, and then the distances are calculated from each cluster center to every pixel in the image. In local KMC, however, the search space of a cluster center is limited to a local 2S×2S square region. Therefore, the SLIC only computes distances from each cluster center to pixels within its searching area.

In local KMC, Euclidean distance is used in the clustering. Let zi be the data of the i-th cluster center with its spatial position as $(x_i, y_i)$. Let $z_j$ be the intensity of a pixel within the search area of the center. Then, the integrated distance between this pixel and the center is:

$$D_I = \sqrt{(d_f/m)^2 + (d_s/S)^2} \qquad \text{(Eq. 2)}$$

where $$d_f = |z_i - z_j|$$

and $$d_s = \sqrt{(x_i - x_j)^2 + ((y_i - y_j)^2)}$$

are the intensity and spatial distances between the pixel and the center, respectively, and m is a regularization parameter that weights the relative contribution of df and ds to the integrated distance Di. A larger m indicates that ds is more significant than $d_f$. An equivalent integrated distance Di directly describing the contribution of the two distances can be given by:

$$D_I = \sqrt{w(d_f/N_f)^2 + (1-w)(d_s/S)^2} \qquad \text{(Eq. 3)}$$

where $N_f$ is the mean intensity of the whole image, $w \in [0,1]$ is a regularization parameter. In this context, w and (1−w) are the ratios of the normalized intensity and spatial distances in $D_i$, respectively.

In some embodiments, the parameter k of the SLIC algorithm specifies the number of approximately equally sized superpixels. In some embodiments, the compactness parameter m can be set to control the trade-off between superpixels' homogeneity and boundary adherence. Without wishing to be bound by any particular theory, it is believed that by varying the compactness parameter, regular-shaped superpixels may be generated in untextured regions and highly irregular superpixels may be generated in textured regions. Again, without wishing to be bound by any particular theory, it is believed that the parameter m also allows for the weighting of the relative importance between color similarity and spatial proximity. When m is large, spatial proximity is more important and the resulting superpixels are more compact (i.e. they have a lower area to perimeter ratio). When m is small, the resulting superpixels adhere more tightly to image boundaries, but have less regular size and shape.

In some embodiments, both pixel size and compactness parameters are adjusted. In some embodiments, a pixel size ranging from between about 40 pixels and about 70 pixels is used. In other embodiments, a pixel size ranging from between about 60 pixels and about 100 pixels is used. In yet other embodiments, a pixel size ranging from between about 70 pixels and about 100 pixels is used. In yet further embodiments, a pixel size ranging from between about 80 pixels and about 100 pixels is used.

Spot Estimation Module

A spot estimation module 208 is utilized in quantifying an amount of stain corresponding to a biomarker in any signal aggregate or blob (step 340). In some embodiments, the estimation module 208 is utilized to determine an amount of signal in each signal aggregate or blob in each of a plurality of sub-regions in an input image, such as sub-regions returned after performing the segmentation module.

In some embodiments, the estimation is based on the linear relationship between the summation of the optical density for the single spots and the aggregate signals, as follows:

$$N = \frac{\sum OD_A}{\sum OD_S}$$

where N is the number of the spots within an aggregate signal region, $OD_A$ is the optical density of the aggregate signals, and $OD_S$ is the computed optical density of a representative isolated spot (from step 401).

In some embodiments, the optical density of a spot aggregate is a measured intensity of the spot aggregate from an input image, such as a from a residual image.

Once the number of predictive spots in each sub-region is estimated (step 340), the data may be stored (step 350) in a database or other storage module 240. In some embodiments, the number of predictive spots for each signal aggregate blob is stored along with the coordinates (x,y) of the blob (such as x,y coordinates of a seed center of the blob). In some embodiments, the detected isolated spots are also stored along with their x,y coordinates as noted herein. In some embodiments, the total number of spots, i.e. the actual detected isolated spots and the predictive spots, for each sub-region are stored.

Figure 15:
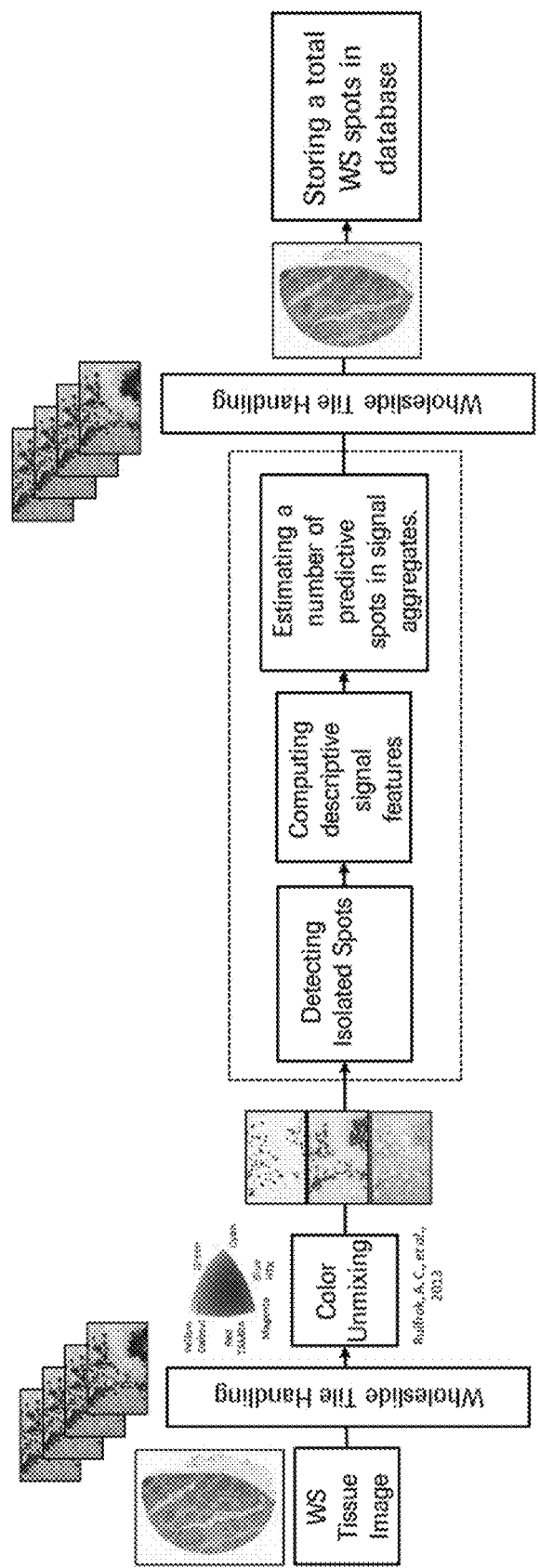
FIG. 15 sets forth an alternative flowchart illustrating steps of estimating signal corresponding to at least one biomarker in a whole slide image in accordance with some embodiments of the present disclosure.

With reference to FIG. 15, in embodiments where several portions of a whole slide image are evaluated independently, the estimated number of predictive spots or the total number of spots (described above) may be stored (step 350) for each portion of the whole slide image. Alternatively, and again with reference to FIG. 15, in embodiments where several portions of a whole slide image are evaluated independently, the estimated number of predictive spots or the total number of spots (described above) in each portion of the whole slide image may be combined such that data corresponding to signal quantity may be stored (step 350) and/or reported (step 360) for the whole slide image.

In some embodiments, a total number of spots for each sub-region may be calculated and stored in a database. For example, a total number of detected isolated spots may be combined (i.e. summed) with the estimated number of predictive spots for each sub-region to provide for the total number of spots for each sub-region.

Figure 17A:
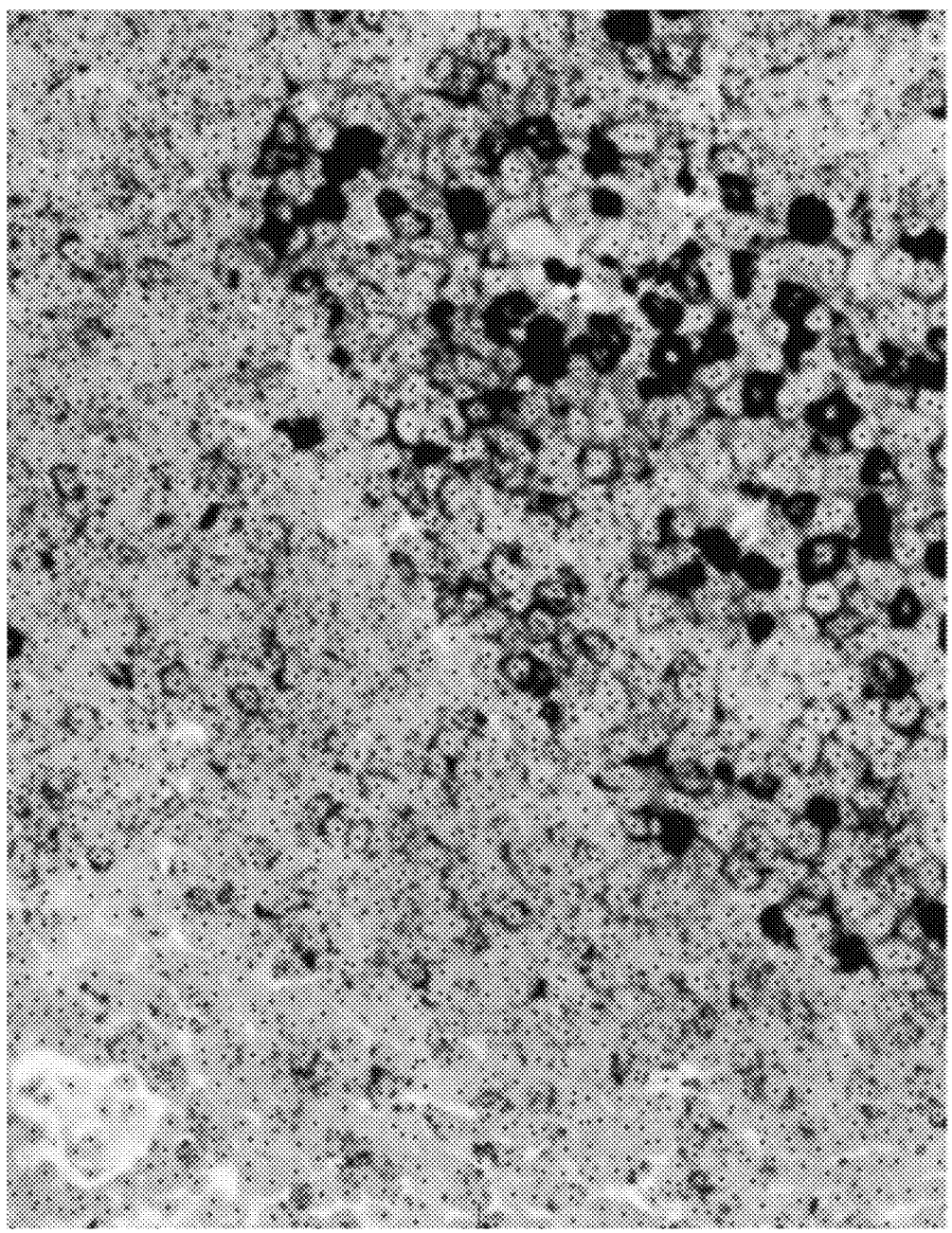
FIG. 17A illustrates the result of nucleus segmentation in accordance with some embodiments of the present disclosure.
Figure 17B:
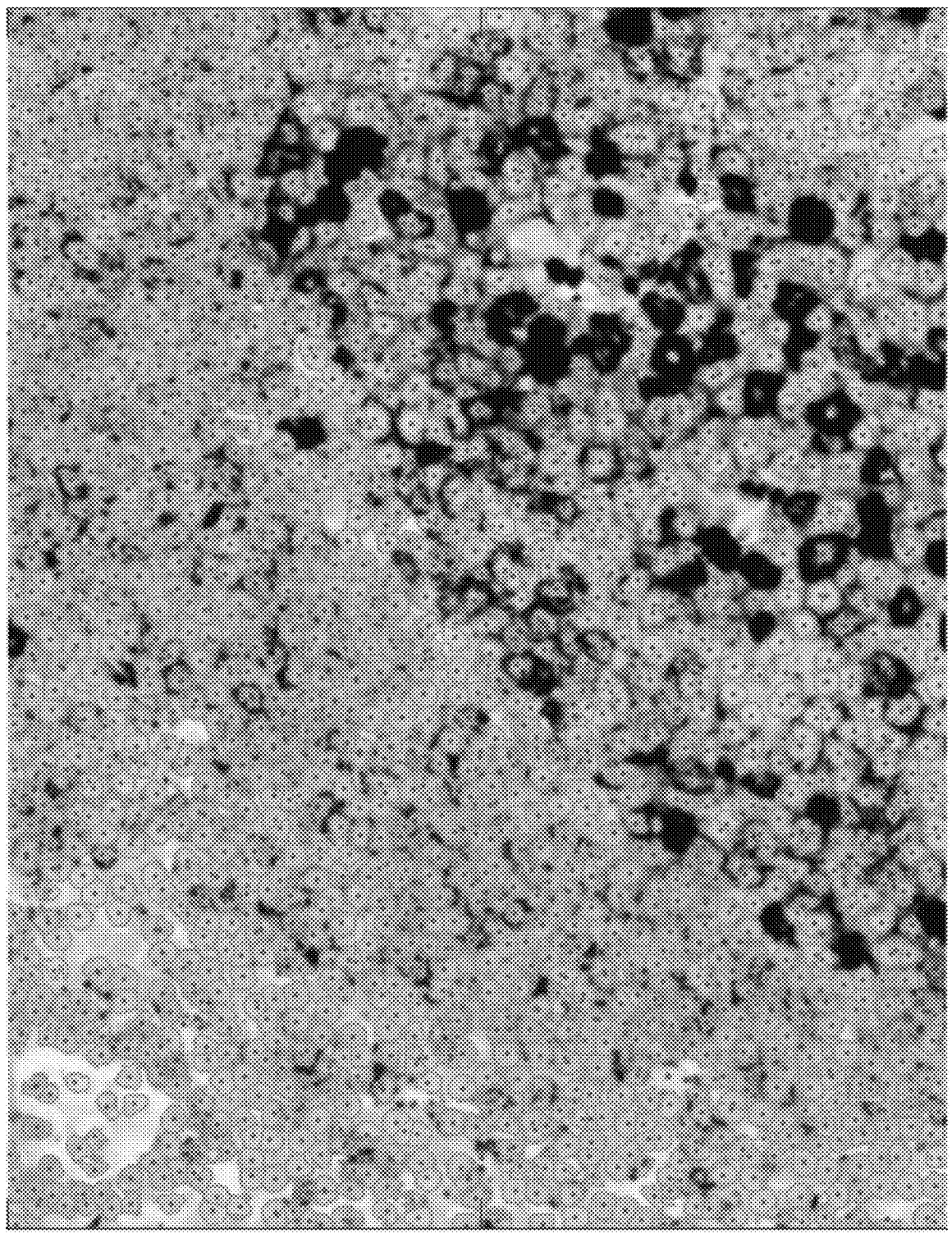
FIG. 17B illustrates the nucleus boundary of each cell in accordance with some embodiments of the present disclosure.

In some embodiments, a total number of spots per cell may be calculated. In some embodiments, a nucleus segmentation may be performed to return a total cell count. After a total number of spots for each sub-region is calculated (such as described above), that result is used along with the total cell count: a total spot count per cell=a total spot count/a total cell count. FIGS. 17A and 17B show the examples of the nucleus segmentation of seed centers (FIG. 17A) and the nucleus boundary of each cell (FIG. 17B).

Overlay Generation Module

Figure 16A:
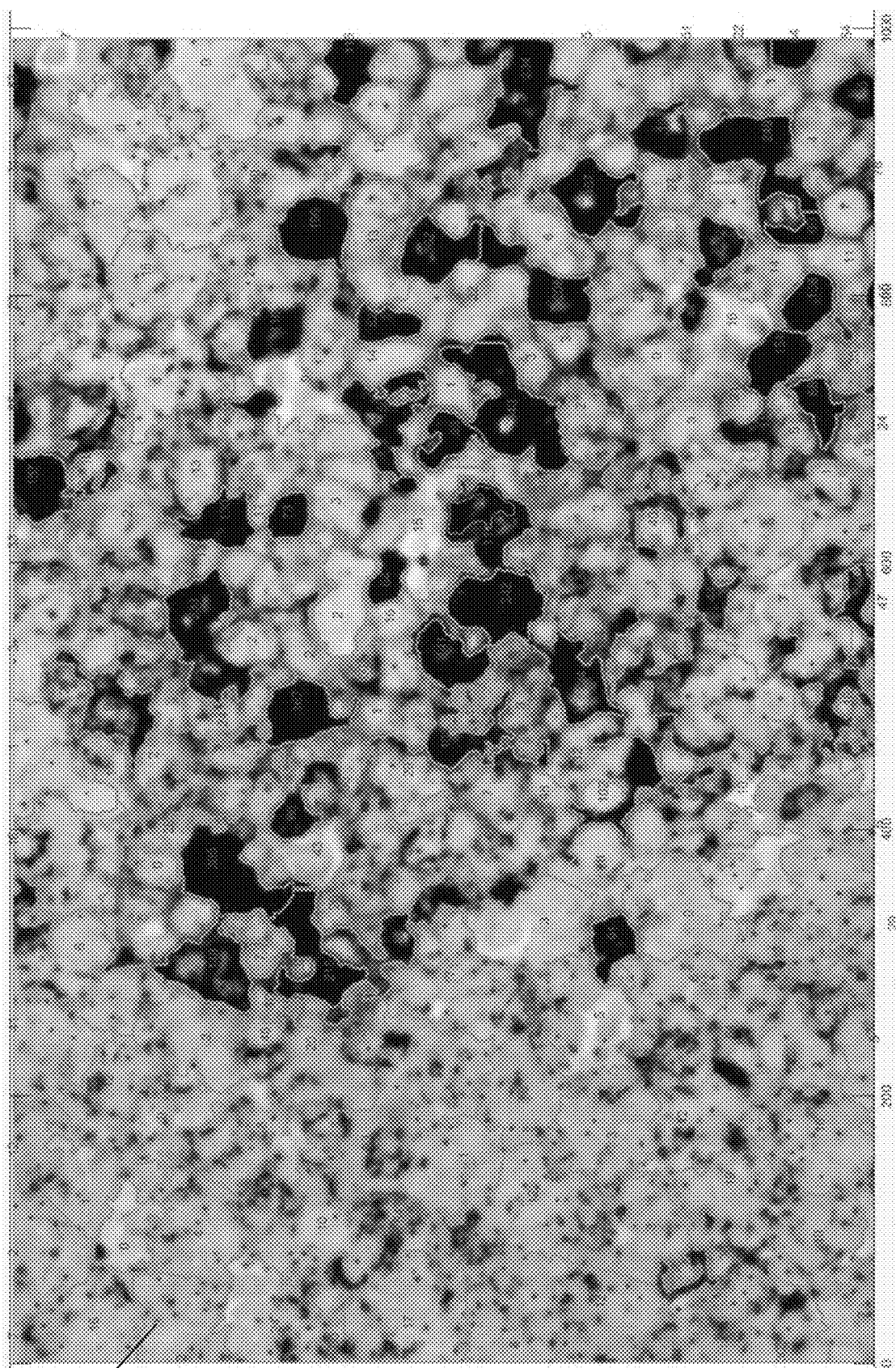
FIGS. 16A and 16B illustrate the result of superimposing detected isolated spots and estimated signal quantities in signal aggregates onto a whole slide image in accordance with some embodiments of the present disclosure.
Figure 16B:
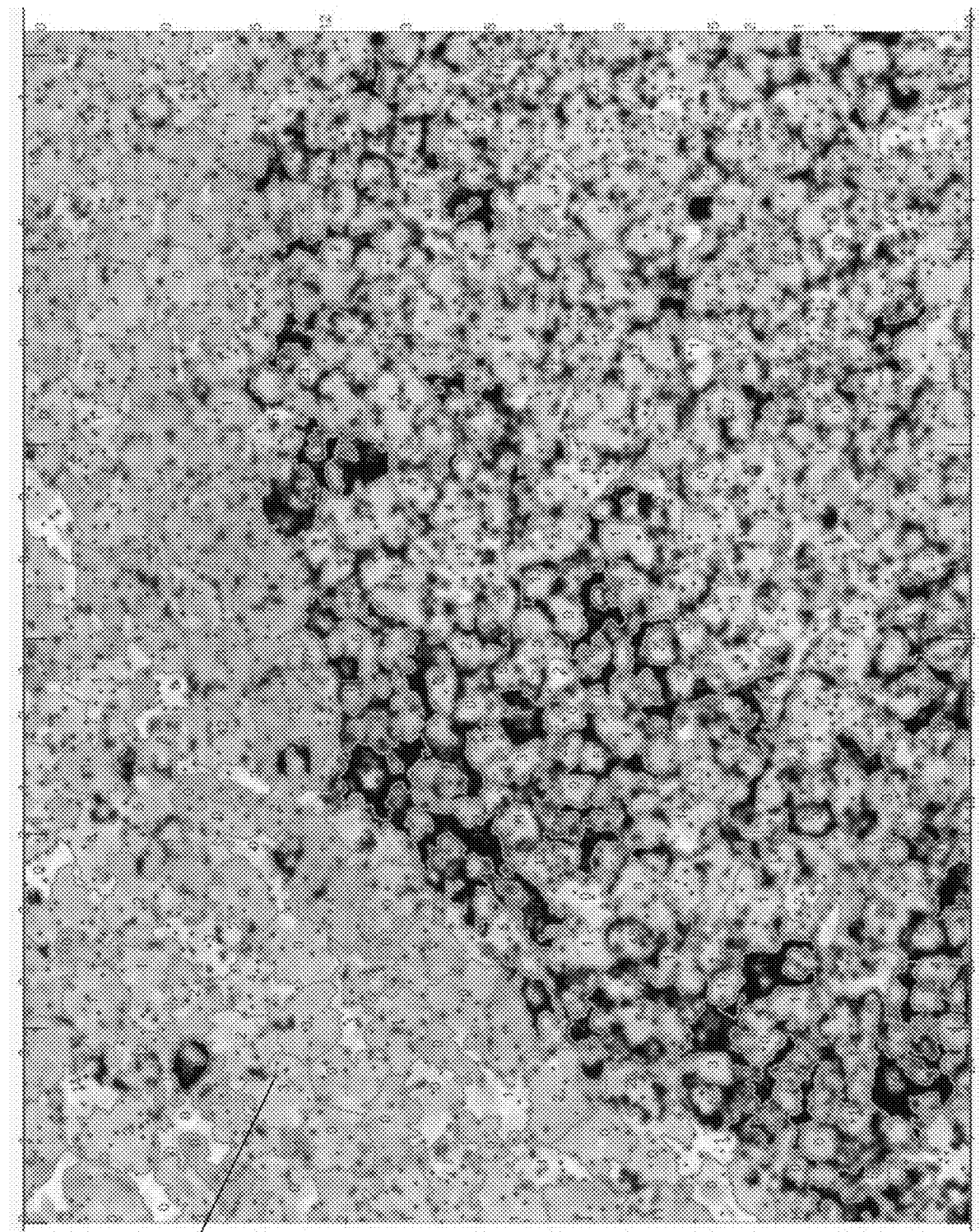

After the isolated spots are detected (step 320) and after the number of predictive spots is estimated (step 340), the data (e.g. the quantitative data) may be reported, such as by superimposing the data onto a whole slide image or a portion thereof. In some embodiments, an overlay generation module 209 is used to compute an overlay which may be subsequently superimposed over an input image. FIGS. 16A and 16B provide examples of suitable overlays where individual detected spots (red dots, 1610) and the estimate number of predictive spots (integer value) for each sub-region are superimposed over a portion of a whole slide image.

In some embodiments, a total number of spots for each sub-region may be calculated and stored in a database (e.g. storage module 240) or depicted visually in an overlay. For example, a total number of detected isolated spots may be combined (i.e. summed) with the estimated number of predictive spots for each sub-region to provide for the total number of spots for each sub-region. Said another way, Total spot count=detected isolated spot count+estimated aggregate signal count.

As an alternative to displaying isolated spots and/or an integer representing the estimated quantity of signal per signal aggregate blob, each sub-region may be color coded to show a total density of detected and predicted spot signals. For example, where a number of total spots would be less than 5, that region may be depicted in blue; where a number of total spots would be between 6 and 15, that region may be depicted in yellow; and where a number of total spots would be greater than 15, that region may be depicted in red.

In addition, when the quantity of signal is estimated for more than one biomarker, e.g. estimating signal corresponding to both the KAPPA and LAMBDA mRNA probes, an overlay may be generated where sub-regions having certain KAPPA to LAMBDA ratios are displayed. For example, the visualization may be a (+) or (−) indicating positivity or negatively for a specific ratio. Likewise, each sub-region may be color coded depending on the derived ratio.

Other Components for Practicing Embodiments of the Present Disclosure

The system 200 of the present disclosure may be tied to a specimen processing apparatus that can perform one or more preparation processes on the tissue specimen. The preparation process can include, without limitation, deparaffinizing a specimen, conditioning a specimen (e.g., cell conditioning), staining a specimen, performing antigen retrieval, performing immunohistochemistry staining (including labeling) or other reactions, and/or performing in situ hybridization (e.g., SISH, FISH, etc.) staining (including labeling) or other reactions, as well as other processes for preparing specimens for microscopy, microanalyses, mass spectrometric methods, or other analytical methods.

The processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized using appropriate deparaffinizing fluid(s). After the paraffin is removed, any number of substances can be successively applied to the specimen. The substances can be for pretreatment (e.g., to reverse protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes.

The specimen processing apparatus can be an automated apparatus, such as the BENCHMARK XT instrument and SYMPHONY instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

After the specimens are processed, a user can transport specimen-bearing slides to the imaging apparatus. In some embodiments, the imaging apparatus is a brightfield imager slide scanner. One brightfield imager is the iScan HT and DP200 (Griffin) brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Publication No. 2014/0178169 filed on Sep. 9, 2011, entitled IMAGING SYSTEMS, CASSETTES, AND METHODS OF USING THE SAME.

The imaging system or apparatus may be a multispectral imaging (MSI) system or a fluorescent microscopy system. The imaging system used here is an MSI. MSI, generally, equips the analysis of pathology specimens with computerized microscope-based imaging systems by providing access to spectral distribution of an image at a pixel level. While there exists a variety of multispectral imaging systems, an operational aspect that is common to all of these systems is a capability to form a multispectral image. A multispectral image is one that captures image data at specific wavelengths or at specific spectral bandwidths across the electromagnetic spectrum. These wavelengths may be singled out by optical filters or by the use of other instruments capable of selecting a pre-determined spectral component including electromagnetic radiation at wavelengths beyond the range of visible light range, such as, for example, infrared (IR).

An MSI system may include an optical imaging system, a portion of which contains a spectrally-selective system that is tunable to define a pre-determined number N of discrete optical bands. The optical system may be adapted to image a tissue sample, illuminated in transmission with a broadband light source onto an optical detector. The optical imaging system, which in one embodiment may include a magnifying system such as, for example, a microscope, has a single optical axis generally spatially aligned with a single optical output of the optical system. The system forms a sequence of images of the tissue as the spectrally selective system is being adjusted or tuned (for example with a computer processor) such as to assure that images are acquired in different discrete spectral bands. The apparatus may additionally contain a display in which appears at least one visually perceivable image of the tissue from the sequence of acquired images. The spectrally-selective system may include an optically-dispersive element such as a diffractive grating, a collection of optical filters such as thin-film interference filters or any other system adapted to select, in response to either a user input or a command of the pre-programmed processor, a particular pass-band from the spectrum of light transmitted from the light source through the sample towards the detector.

An alternative implementation, a spectrally selective system defines several optical outputs corresponding to N discrete spectral bands. This type of system intakes the transmitted light output from the optical system and spatially redirects at least a portion of this light output along N spatially different optical paths in such a way as to image the sample in an identified spectral band onto a detector system along an optical path corresponding to this identified spectral band.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Any of the modules described herein may include logic that is executed by the processor(s). "Logic," as used herein, refers to any information having the form of instruction signals and/or data that may be applied to affect the operation of a processor. Software is an example of logic.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks). For example, the network 20 of FIG. 1 can include one or more local area networks.

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Example

Figure 18:
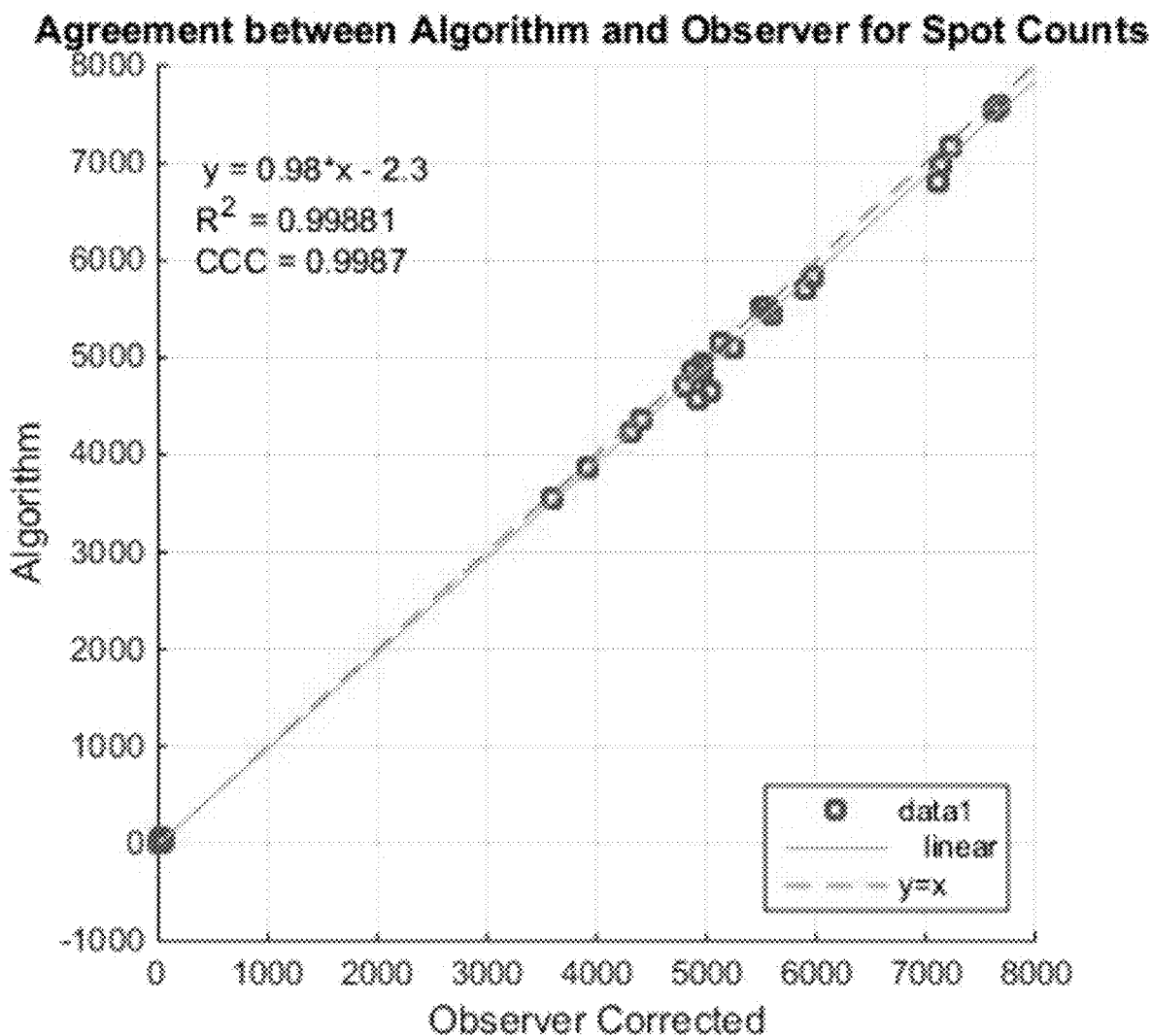
FIG. 18 illustrates the overall scatter of the spot count agreement between expert observer and the algorithm results ($R^2$=0.99, CCC=0.99) verified on 31 fields of view. The plot shows a good distribution of spot counts with a slope of 0.98 and an interception of −2.3. The total spot counts identified by the observer (126,588) and the algorithm (124,040) is illustrated in the accompanying table.

Quality control was performed based on a graphic user interface (GUI) which the detected isolated spots overlaid on the original and the observer could correct e.g. add, delete, move the spots. The verification was performed using 31 FOV on the simplex silver images by an expert observer (scientist). The agreement plot is shown below with the $R^2$ of 0.99 and CCC=0.99. The example of the spot counting results before and after the correction is in FIG. 18.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

What is claimed:

1. A method of estimating an amount of signal corresponding to at least one biomarker in an image of a biological sample comprising:
   (a) detecting isolated spots in a first image;
   (b) deriving an optical density value of a representative isolated spot based on signal features from the detected isolated spots;
   (c) estimating a number of predictive spots in signal aggregates in each of a plurality of sub-regions based on the derived optical density value of the representative isolated spot; and
   (d) storing the estimated number of predictive spots and detected isolated spots in each of the plurality of generated sub-regions in a database,
   wherein the number of predictive spots in the signal aggregates in each of the plurality of the sub-regions is estimated by calculating a quotient of a total optical density of the signal aggregates in one of the sub-regions divided by the derived optical density of the representative isolated spot.

2. The method of claim 1, wherein the optical density of the representative isolated spot is derived by: (i) generating histogram plots from computed descriptive signal features from all of the detected isolated spots; (ii) extracting size and intensity parameters from the histogram plots; (iii) calculating an area measurement from the extracted size parameters; and (iv) multiplying the extracted intensity parameter by the calculated area measurement.

3. The method of claim 1, wherein the estimation of the number of the predictive spots in the signal aggregates is performed using a second image which is substantially free from signals corresponding to the detected isolated spots.

4. The method of claim 3, wherein the second image is derived by (i) generating a foreground segmentation mask based on the detected isolated spots in the first image; and (ii) filtering the first image with the generated foreground segmentation mask.

5. The method of claim 3, wherein the second image is generated by (i) generating an isolated spots image including only the detected isolated spots from the first image; and (ii) subtracting the isolated spots image from the first image.

6. The method of claim 1, wherein each sub-region of the plurality of sub-regions has pixels which are substantially uniform in at least one of biomarker staining intensity, biomarker staining presence, and local biomarker staining texture.

7. A system for estimating an amount of one or more signals in a biological sample, the one or more signals corresponding to stained targets in the biological sample, the system comprising:
   (i) one or more processors, and (ii) a memory coupled to the one or more processors, the memory to store computer-executable instructions that, when executed by the one or more processors, cause the system to perform operations comprising:
      (a) detecting isolated spots in a first image;
      (b) computing descriptive signal features from all detected isolated spots;
      (c) estimating a number of predictive spots in signal aggregates in each of a plurality of sub-regions in a second image based on the computed descriptive signal features; and
      (d) storing at least the estimated number of predictive spots in the memory,
   wherein the number of predictive spots in the signal aggregates in each of the plurality of the sub-regions is estimated by:
      (i) deriving an optical density of a representative isolated spot, the optical density of the representative isolated spot derived from the computed descriptive signal features; and
      (ii) calculating a quotient of a total optical density of the signal aggregates in one of the sub-regions of the second image divided by the derived optical density of the representative isolated spot.

8. The system of claim 7, wherein the optical density of the representative isolated spot is derived by:
   (i) generating histogram plots from each of the computed descriptive signal features;
   (ii) extracting size and intensity parameters from the histogram plots;
   (iii) calculating an area measurement from the extracted size parameters; and
   (iv) multiplying the extracted intensity parameter by the calculated area measurement.

9. The system of claim 7, wherein the intensity parameter is a uniform intensity metric or a non-uniform intensity metric.

10. The system of claim 7, wherein the size parameter is a mode of a radius from a full width at half maximum histogram.

11. The system of claim 7, wherein the first image is a first unmixed image channel image corresponding to signals from a first biomarker.

12. The system of claim 7, wherein the estimation of the number of the predictive spots in the signal aggregates is performed using a second image which is substantially free from signals corresponding to the detected isolated spots.

13. A non-transitory computer-readable medium storing instructions for estimating amounts of different signals in a stained biological sample comprising:
   (a) detecting isolated spots in a first image;
   (b) deriving an optical density value of a representative isolated spot based at least on intensity and size signal features from the detected isolated spots; and
   (c) estimating a number of predictive spots in signal aggregates in each of a plurality of sub-regions in a second image based on the derived optical density value of the representative isolated spot,
   wherein the number of predictive spots in the signal aggregates in each of the plurality of the sub-regions is estimated by calculating a quotient of a total optical density of the signal aggregates in one of the sub-regions divided by the derived optical density of the representative isolated spot.

14. The non-transitory computer-readable medium of claim 13, wherein the optical density of the representative isolated spot is derived by:
   (i) generating histogram plots from each of the signal feature from the detected isolated spots;
   (ii) extracting size and intensity parameters from the histogram plots;
   (iii) calculating an area measurement from the extracted size parameters; and
   (iv) multiplying the extracted intensity parameter by the calculated area measurement.

15. The non-transitory computer-readable medium of claim 13, wherein the isolated spots are detected using a shape-detector having a disk-like shape.

16. The non-transitory computer-readable medium of claim 13, wherein the sub-regions are superpixels.

17. The non-transitory computer-readable medium of claim 16, wherein the superpixels are derived by (i) grouping pixels with local k-means clustering; and (ii) using a connected components algorithm to merge small isolated regions into nearest large superpixels.

* * * * *